United States Patent
Stephens et al.

[19]

[11] Patent Number: 5,977,691
[45] Date of Patent: Nov. 2, 1999

[54] ELEMENT INTERCONNECTIONS FOR MULTIPLE APERTURE TRANSDUCERS

[75] Inventors: Thomas P. Stephens, Alton, N.H.; Matthew Mooney, Westford; William J. Ossmann, Acton, both of Mass.; Larry Pendergrass, Santa Rosa, Calif.

[73] Assignee: Hewlett-Packard Company, Palo Alto, Calif.

[21] Appl. No.: 09/021,596

[22] Filed: Feb. 10, 1998

[51] Int. Cl.⁶ ................................................. H01L 41/08
[52] U.S. Cl. ........................................................... 310/334
[58] Field of Search ................................. 310/334–337

[56] References Cited

U.S. PATENT DOCUMENTS

| | | | |
|---|---|---|---|
| 3,496,617 | 2/1970 | Cook et al. | 310/334 |
| 3,587,561 | 6/1971 | Ziedonis | 128/2.05 |
| 3,718,898 | 2/1973 | Cook et al. | 310/334 |
| 3,952,387 | 4/1976 | Iinuma et al. | 29/25.35 |
| 4,117,074 | 9/1978 | Tiersten et al. | 310/320 |
| 4,211,948 | 7/1980 | Smith et al. | 310/322 |
| 4,211,949 | 7/1980 | Brisken et al. | 310/322 |
| 4,217,684 | 8/1980 | Brisken et al. | 29/25.35 |
| 4,281,550 | 8/1981 | Erikson | 310/334 X |
| 4,371,805 | 2/1983 | Diepers et al. | 310/334 |
| 4,385,255 | 5/1983 | Yamaguchi et al. | 310/335 |
| 4,404,489 | 9/1983 | Larson, III et al. | 310/334 |
| 4,462,092 | 7/1984 | Kawabuchi et al. | 310/334 |
| 4,470,308 | 9/1984 | Hayakawa et al. | 310/334 |
| 4,479,069 | 10/1984 | Miller | 310/334 X |
| 4,576,045 | 3/1986 | Miller-Jones | 310/334 X |
| 4,638,468 | 1/1987 | Francis | 310/334 X |
| 4,686,408 | 8/1987 | Ishiyama | 310/334 |
| 4,734,963 | 4/1988 | Ishiyama | 310/317 X |
| 4,747,192 | 5/1988 | Rokurota | 310/334 X |
| 5,311,095 | 5/1994 | Smith et al. | 310/334 |
| 5,493,541 | 2/1996 | Snyder | 310/334 X |
| 5,629,578 | 5/1997 | Winzer | 310/334 |
| 5,744,898 | 4/1998 | Smith et al. | 310/334 |

FOREIGN PATENT DOCUMENTS 1530783  11/1978  United Kingdom .

*Primary Examiner*—Mark O. Budd

[57] ABSTRACT

A multiple aperture ultrasonic transducer having a linear array of elements, each element having a plurality of segments forming apertures of the array, and a connection assembly for interconnecting the segments and connecting the segments to circuits. The connection assembly includes an electrode layer directly adjacent to the segments, at least one insulating layer, and at least one connector layer. The electrode layer has an electrode area for each segment and one of the insulating layers has a connection opening for each segment and connection areas for pairs of segments while the connection layer has segment to segment connectors and segment pad connectors. Each element may be divided into sub-elements with connection cross-overs offset by one sub-element along the array and alternately reversed while alternate middle segments connect to alternate sides. The connection assembly may include interlayer connector layer and may be constructed onto a carrier which may be removed before attachment to a backing body, or the connection assembly may be deposited onto the array before attachment to a backing body. The connection assembly may be fabricated as a single assembly with a monolithic block of piezoelectric material and the assembly diced to a predetermined depth and across a predetermined width so that selected connections between electrode areas and to the pads remain intact. Interlayer vias are staggered and have clearance openings extending into the dicing kerf to reduce space and to insure connection after dicing.

10 Claims, 11 Drawing Sheets

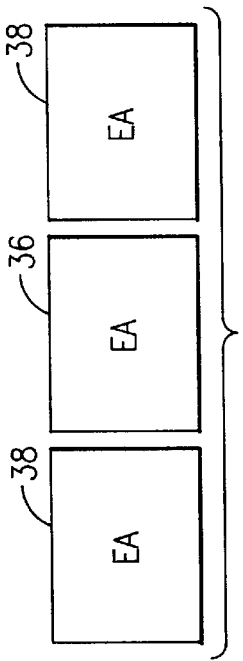
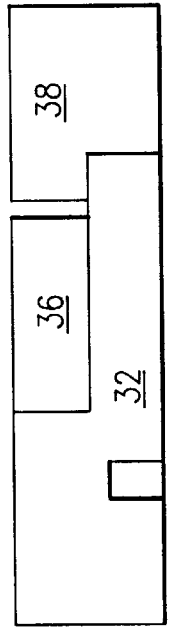
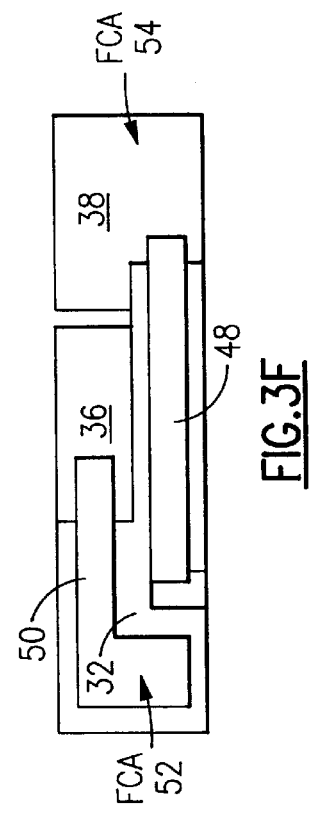
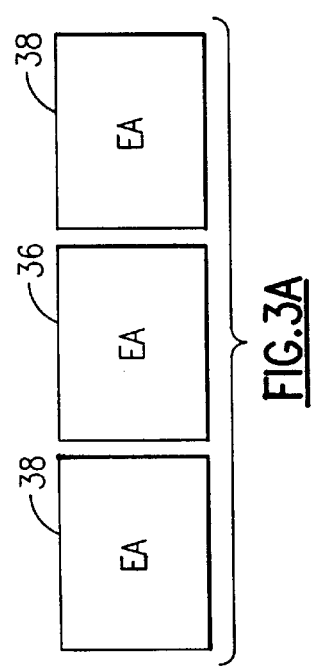
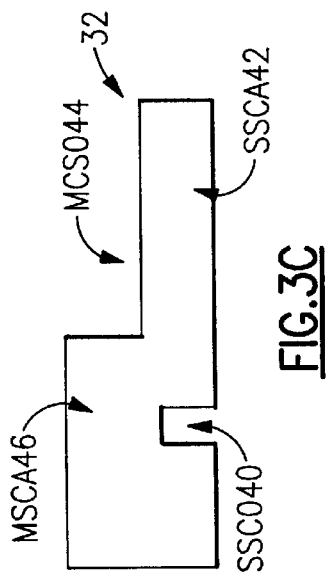

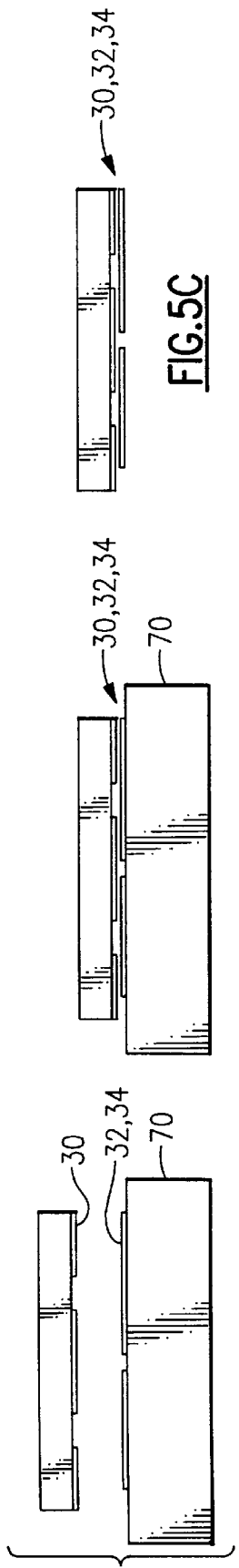
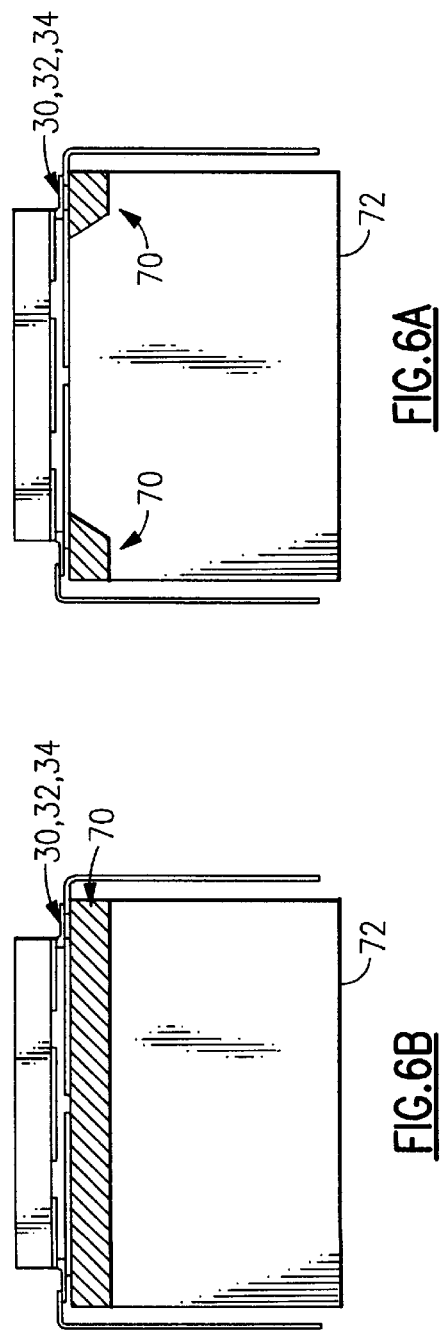

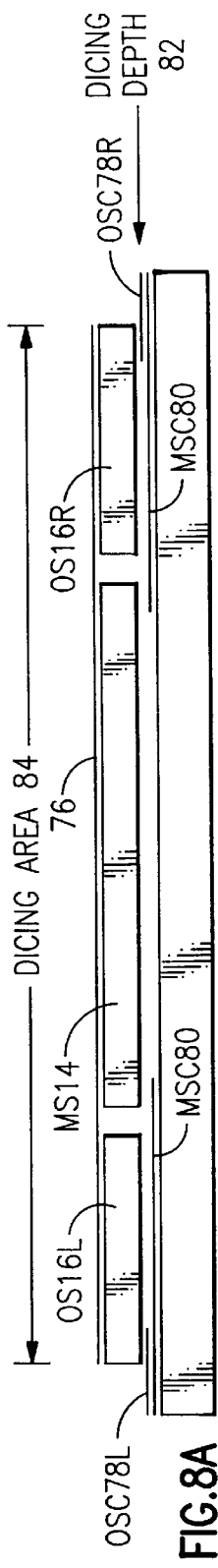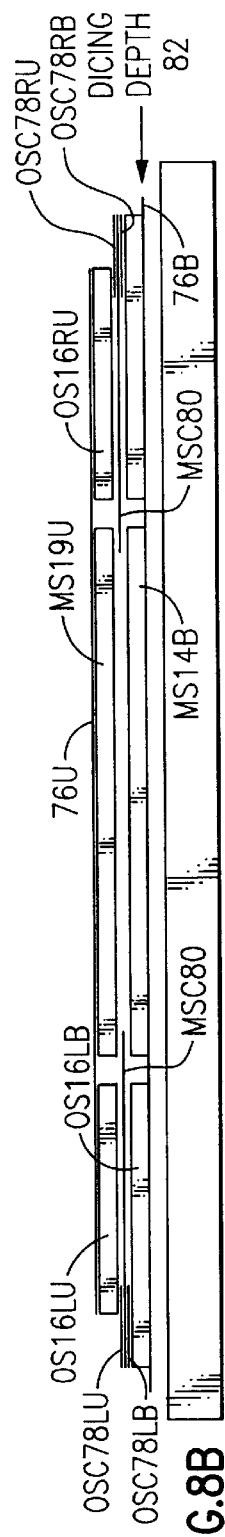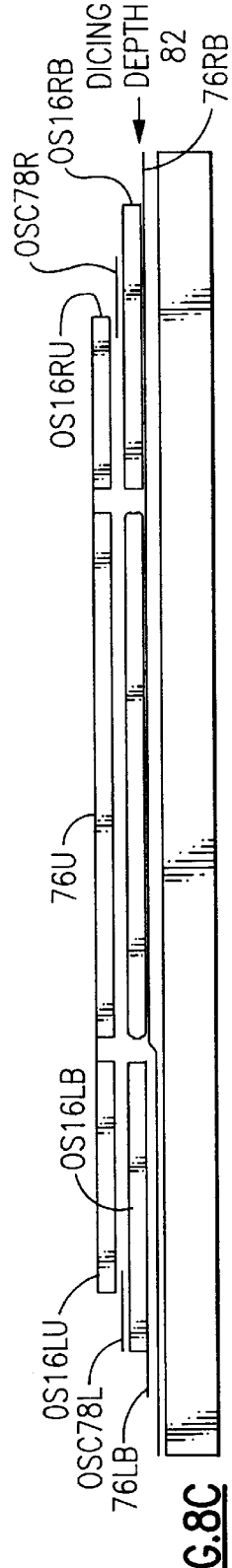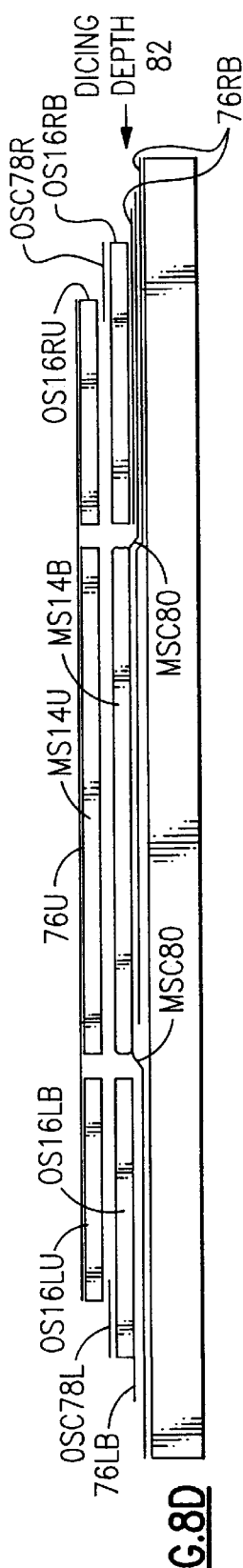

ELEMENT INTERCONNECTIONS FOR MULTIPLE APERTURE TRANSDUCERS

FIELD OF THE INVENTION

The present invention relates to a design and the method of constructing ultrasonic transducers and, in particular, multiple aperture transducers.

BACKGROUND OF THE INVENTION

Ultrasonic transducers are used in many medical applications and, in particular, for the non-invasive acquisition of images of organs and conditions within a patient, typical examples being the ultrasound imaging of fetuses and the heart. The ultrasonic transducers used in such applications are generally hand held, and must meet stringent dimensional constraints in order to acquire the desired images. For example, it is frequently necessary that the transducer be able to obtain high resolution images of significant portions of a patient's chest cavity through the gap between two ribs when used for cardiac diagnostic purposes, thereby severely limiting the physical dimensions of the transducer.

As a consequence, and because of the relatively small aperture between human ribs and similar constraints upon transducer positioning when attempting to gain images of other parts of the human body, there has been significant development of linear or phased array transducers comprising multiple transmitting and receiving elements, with the associated electronics and switching circuits, to provide relatively narrowly focused and "steerable" transmitting and receiving "beams". The most common of such transducers comprises a one element wide by multiple element long linear array of transmitting and receiving elements, thereby allowing the beam to be focused and scanned along the plane of the transducer elements, which is referred to as azimuth scanning. The elements of such transducers are often arranged in line along a flat plane or may be arranged along concave or convex contours, thereby providing a greater scanning arc, and are often provided with acoustic focusing lenses made of materials having suitable properties to act as lenses in the acoustic frequency ranges of interest.

The transducer elements of linear or phased array transducers are most frequently made of a piezoelectric material and the linear array of elements is generally mounted onto a body made of some backing material. One or more layers of impedance matching material, generally considered to be a part of the elements themselves, is often superimposed upon the transducer elements. A lens comprised of a suitable material may be additionally superimposed upon the impedance matching material to shape or focus the beams generated by the transducer elements, or the impedance matching material may have suitable characteristics and may be shaped to operate as an acoustic lens. Connections between the individual transducer elements and the associated electronics and switching elements are usually provided through various arrangements and combinations of thick and thin film circuits, flexible printed circuits and wires.

Such transducers are generally constructed from a single piece of transducer material having a width equal to the length of one element and a length equal to the widths of the total number of elements plus spaces between the elements. One or more thin or thick film circuits or flexible printed circuits having connections and paths for the individual elements, or the like implemented in any of several other ways, are bonded to one side of the piece of transducer material and a layer or layers of matching material may be bonded to the stack as required by the final construction of the transducer. A temporary or permanent layer of backing material of some form, such as a flexible material, may also be bonded to the back of the stack to aid in handling the stack during manufacture.

Successive cuts are then made across the width of the transducer stack at intervals corresponding to the widths of the elements and the spacing between the elements to divide the single piece of material into the individual elements. This operation is generally referred to as "dicing" and is usually done with a device referred to as a dicing saw, but may be done with other techniques, such as lasers. These cuts may extend only through the transducer and matching material layers, or partly or completely through the circuit layer, or through the circuit layer and at least a part of any backing layers, depending upon the detailed design and implementation of the circuit layers. The assembly of individual transducer elements with the circuit and matching layers are then bonded to the backing body, which may have a flat, concave or convex face, as described above, with any temporary backing layers being removed as necessary. It should be noted that in certain instances the dicing may be done after the assembly of transducer elements, matching materials, and circuits is bonded to the backing material and that the dicing cuts may extend into the layers of backing material or even into the backing body.

The connections to wires or printed circuits, such as flexible circuits, which in turn connect to the electronics and switching elements are made before or after the transducer assembly is bonded to the backing body, again depending on the detailed design and implementation of these connections.

While such azimuth scanning linear or phased arrays are advantageous for the intended purposes of such ultrasonic transducers, this type of linear or phased array transducer has the disadvantage that it can perform only an azimuth scan along the single plane of the transducer elements and is thereby often referred to as a one dimensional, or "1D", array. As a consequence, there have been many attempts to provide linear or phased array transducers that are also capable of scanning or focusing in elevation as well as azimuth, that is, along the axis at right angles to the azimuth plane along which the elements are arrayed, as well as along the azimuth plane.

As is well understood, the formation, steering and focusing of the transmitting and receiving beams of a transducer are controlled by selection and use of the various separate physical divisions or areas of transducer material comprising the transducer array, which are referred to as apertures. In a "1D" array, which is capable of forming beams only along the azimuth scan plane, each transducer element forms a single aperture, so that the array is formed of a single row of apertures extending along the face of the array, and such transducers are referred to as "single aperture" transducers.

In contrast with a "single aperture" transducer, in which each aperture is formed by an element extending across the face of the array as a single unitary area or division, each corresponding element in a transducer capable of scanning in elevation is divided into multiple sub-areas, or elevation sub-segments, and thereby into multiple apertures. Such transducers are consequently referred to as "multiple aperture" transducers, or two dimensional or "2D" transducers. The shape, focus and direction of the scan planes and beams of a multiple aperture transducer are again controlled by selecting combinations of the apertures, that is, of the sub-areas of the transducer elements, so that the apertures of a multiple aperture array can be used to steer and focus the transducer scan beam along the elevation axis as well as along the azimuth axis and can define multiple azimuthal scan planes, each being at a different angle of elevation. The apertures may be either driven actively, or simply de-activated to reduce the size of the acoustic aperture, thereby controlling the shape, direction and focus of the transmitting and receiving beams formed by the transducer array.

While the construction of the piezoelectric elements for a multiple aperture transducer presents greater difficulties than for a single aperture array, the methods are well known and similar to those used in construction of a single aperture array. For example, a particular application may require that each element be comprised of three segments, or apertures, that is, two outer segments and a middle segment. This may be achieved, for example, by constructing the transducer elements from three elongated pieces of transducer material, that is, two outer pieces and a middle piece, and then dicing the pieces across the face of the array as was described with regard to single aperture arrays, or by additional cuts along the transducer stack in the longitudinal direction to divide the two outer segments from the middle segment.

The primary problem in constructing multiple aperture arrays is that the number of electrical connections to each element, each of may be comprised of three or more segments, and possibly between elements, is greatly increased while the space in which to make the connections does not increase. For example, going from a single aperture array to a three aperture array triples the number of segments in each elements, that is, from one to three, and, instead of one connection to the single segment comprising the element, there must be two separate connections to the two outer segments, a third connection to the middle segment, and additional connections to each possible pair of segments. In addition, each middle segment is bounded on both ends by the outer segments of the element and on either side by the two adjacent elements, so that the middle segments are not readily accessible for connections. In addition, the connections to the outer and middle segments must be made in such a manner as not to interfere with the acoustic characteristics of the transducer.

Considering a specific example, the Hewlett-Packard Model 21215 transducer provides two sizes of elevation apertures and is constructed generally as described above, that is, of a linear array of separate or separated elements wherein each element is comprised of three separate segments, two outer segments and a middle segment. In this design, the elements are arranged in a straight plane, rather than a concave or convex arc, and the middle segment of each element is connected to a transmit/receive circuit while the two outer segments of the element are connected together and then to a second transmit/receive circuit or through a switch to the same transmit/receive circuit as the middle segment.

Connections to the segments are made through flex circuits, that is, circuits etched onto thin, flexible circuit boards, and an individual flex circuit is used for each set of elevation segment connections wherein each flex circuit contains all of the connections for the corresponding segments of each of the elements along the array. The transducer therefore requires three flex circuits, one for each out row of segments and one for the middle row of segments. The two flex circuits connecting to the outer segments of each element of the outer segments and are then connected by a jumper flex circuit or a circuit board. The third flex circuit connects to the middle segments of the elements, and thus must make connection at the middle of the back side of the piezoelectric array.

It is therefore apparent that a two aperture array requires three times as many connections to the piezoelectric segments themselves, twice as many flex circuits as in a single aperture array, and two additional flex circuit to flex circuit connections by a flex jumper or printed circuit board for each element. These connections result in higher cost and lower manufacturing yield and reliability. In addition, assembly is more complex in that the flex circuit to the middle segments must be carefully aligned with the flex circuits to the outer segments. This factor alone makes it difficult, if not impossible, to manufacture a curved array and the presence of the middle segment flex circuit requires the user of either a poured backing body material or complex molding or machining to manufacture the backing body.

The methods used in the prior art to construct multiple aperture arrays include the use of multiple flex circuits, as described just above, connections embedded in the backing body, and the use of electrostrictive rather than piezoelectric materials for the transducer elements.

The disadvantages of multiple flex circuits have been discussed above, and the disadvantages of connections embedded in the backing body are comparable. For example, a preferred method for embedding connection circuits in the backing body is the use of laminating layers of backing material on or in which signal leads have been made. An alternative is the use of a multi-layer thick film ceramic hybrid circuit which also serves as the backing body. The laminated layers with embedded connection circuits results in leads which run vertically, that is, perpendicularly, between the segments and an interface circuit to which the connections are made, but also results in leads with very small cross sections that are attached at both ends by butt joints, which lack reliability. The use of a multi-layer thick film circuit, in turn, can provide much stronger and more reliable connections, but the acoustic characteristics of the ceramic material degrades the acoustic performance of the transducer. Both approaches, moreover, have the disadvantage of requiring multiple steps to make the connections to the piezoelectric elements and the added cost from not using standard printed or hybrid circuit manufacturing techniques.

Certain other transducer designs have used electrostrictive materials rather than piezoelectric materials for the elements because electrostrictive materials require only one signal lead for each element as the aperture can be controlled by switching entire segments of the elements on or off with a dc bias voltage.

The present invention provides a solution to these and other problems of the prior art.

SUMMARY OF THE INVENTION

The present invention is directed to a multiple aperture ultrasonic transducer having a linear array of transmitting and receiving elements, each element comprising a middle segment and at least one pair of outer segments located about the middle segment wherein the middle and outer segments form apertures of the array, and a connection assembly for interconnecting the outer segments of each element and for connecting the segments of each element to transmit/receive circuits.

According to the present invention, the connection assembly includes, for each element of the array, an electrode layer located directly adjacent to the segments of the element, at least one insulating layer superimposed on the electrode layer, and at least one connector layer superimposed on the at least one insulating layer.

The electrode layer has an electrode area corresponding to each segment of the element with each electrode area being located adjacent to and connecting to the corresponding segment.

At least one of the insulating layers has a segment to segment connection opening corresponding to and located within the electrode area of each outer segment and a segment to segment connection area for and corresponding to each pair of outer segments, each segment to segment connection area extending between the segment to segment connection openings of the pair of outer segments. At least one of the insulating layers also has a middle segment connection opening corresponding to and located within the electrode area of the middle segment and a middle segment connection area extending from the middle segment connection opening and to an edge of the element.

At least one of the connection layers has a middle segment connector connected to the middle segment electrode and extending from the middle segment connection opening and across the middle segment connection area to a pad at the edge of the element to connect to a transmit/receive circuit. At least one of the connection layers also has, for each pair of outer segments, a segment to segment connector extending across the segment to segment connection area of the outer segments and connected to the electrode areas of the outer segments and to a pad at the edge of the element to connect to a transmit/receive circuit.

In certain implementations of the transducer of the present invention each element is divided into sub-elements and the number of cross-overs required in the connection circuits is reduced by a construction wherein one half of the segments of each sub-element and the connection assembly connections thereto are offset along the length of the array by one sub-element relative to the other half of the segments of the sub-element and wherein the order of the pads connecting the middle segment and outer segment conductors to the transmit/receive circuits are correspondingly reversed on alternate sub-elements.

Also, in yet other implementations of the present invention, the middle segment connector of successive elements along the linear array are routed to alternate edges of the linear array, thereby increasing the available space in each element area for routing outer segment conductors.

According to the present invention, the connection assembly can be constructed in a number of ways. In one implementation, the connection assembly is constructed on a carrier, the carrier and connection assembly are assembled to the transmitting and receiving elements, and the carrier and connection assembly are assembled to a backing body so that the carrier is a mechanical and acoustic element of the transducer structures.

In another implementation, the connection assembly is constructed on a carrier, the carrier and connection assembly are assembled to the transmitting and receiving elements, the carrier is removed from the connection assembly, and the connection assembly and transmitting and receiving elements are assembled to a backing body. In yet another implementation, the carrier is first removed from the connection assembly and the connection assembly is assembled to the transmitting and receiving elements and to the backing body.

In still another implementation of the present invention, the electrode, insulating and connector layers are formed by deposition process onto a matching layer carrier comprised of a material having acoustic properties to function as a matching layer of the transducer and the matching layer carrier with the electrode layer, the insulating layer and the connector layer are assembled to a transmitting and receiving face of the transducer to function as a matching layer.

In yet another implementation of the present invention, the electrode, insulating and connector layers are formed by deposition process directly onto the transmitting and receiving elements of the transducer. A backing body or matching layer may then be superimposed onto the connection assembly that has been directly deposited onto the piezoelectric material comprising the transmitting and receiving elements.

In other aspects of the present invention, the elements of the transducer are initially constructed of a monolithic block of transducer element material and the connection assembly is initially fabricated as a single assembly including the electrode layer, insulating layers and connection layers for all elements of the transducer. The connection assembly is then assembled to the monolithic block and the monolithic block of transducer element material is thereafter diced into the individual elements of the linear array by dicing the assembly of the monolithic block and transducer element material and the connection assembly in cross sectional dicing areas bounded by a predetermined dicing depth and across a predetermined dicing width.

According to the present invention, and wherein the transducer elements and connection assembly are fabricated as single units and the sub-divided by dicing, a plurality of vias are used to connect the electrode areas of the segments to the corresponding connectors of the connector layer. The electrode layer and at least portions of the insulating and connector layers are located within the cross sectional dicing areas and reserved areas of the connection assembly are located outside the cross sectional dicing areas, so that the connections formed between the electrode areas of the segments and from the electrode areas to the pads in the connector layer in the portions of the connector layer located in the reserved areas thereby remain intact. Again, the assembly may be constructed of a plurality of either or both of the insulating and connector layers, particularly when the connection layer or layers are formed from ultra thin flexible circuits.

Further with regard to constructing the transducer by dicing of assembled unitary elements, in certain implementations each element of the linear array is comprised of at least two layers of transducer material with an interlayer electrode layer between the layers of transducer material. Interlayer electrode areas are formed in the interlayer electrode layer and connect the middle segments of the elements through interlayer vias with the layers of the connection assembly.

According to the present invention, the interlayer vias are located along the edges of the middle segments to connect with the interlayer electrode layer connecting to the middle segments and are arrayed in staggered patterns so that when the layers of transducer material are diced into the elements of the linear array, at least one interlayer via connected to each middle segment will remain intact.

Finally, according to the present invention certain interlayer vias may remain unconnected to selected layers of the connection assembly by forming clearance holes around the interlayer vias where the interlayer vias pass through the selected layers. According to the present invention, the interlayer vias having clearance holes are located adjacent the edges of the electrode areas so that each clearance hole extends into a dicing kerf between the elements, thereby providing more space in the conductor areas for the necessary conductors.

Other features, objects and advantages of the present invention will be understood by those of ordinary skill in the art after reading the following descriptions of a present implementation of the present invention, and after examining the drawings, wherein:

BRIEF DESCRIPTION OF THE DRAWINGS

FIGS. 3A through 3F are diagrammatic representations of the layers and assembly of a connection assembly for a two aperture transducer;

FIGS. 5A through SC are side views of the assembly of a transducer with a connection assembly carrier;

FIGS. 6A and 6B are side views of the assembly of a transducer with and without a carrier integral with the connection assembly;

FIGS. 8A through 8D are cross section views of a transducer with multiple piezoelectric layers and the connections therefor;

DETAILED DESCRIPTION

The following describes a plurality of constructions and methods of construction for multiple aperture ultrasonic transducers and, in particular, for providing improved techniques accomplishing the interconnections to and between the segments of the piezoelectric elements of ultrasonic transducers. As such, the following description will be divided into several major sections, each section describing an improved technique or an aspect of an improved technique for constructing the interconnections to and between the segments of the piezoelectric elements the transducers.

A. Multi-Layer Backplane Interconnections

Figure 1A:
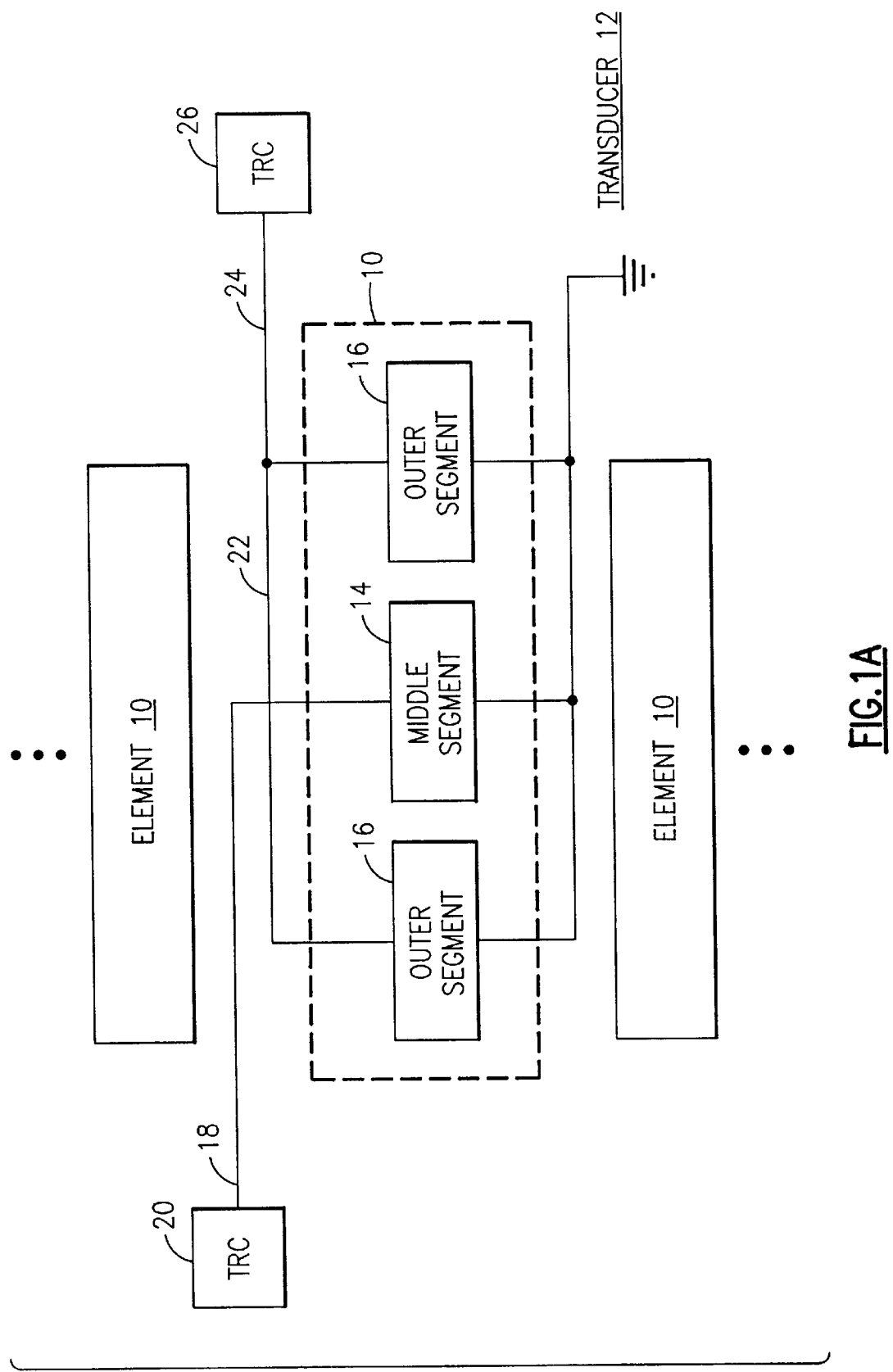
FIG. 1A is an illustration of the segments and connections of a two aperture transducer.

Referring to FIG. 1A, therein is shown a diagrammatic representation of a single piezoelectric Element 10 of a two aperture Transducer 12 and, in outline form, the two adjacent Elements 10 of the linear array of Elements 10 comprising the transmit/receive array of the transducer. As indicated therein in diagrammatic form, the construction of the transducer as a two aperture transducer requires that each piezoelectric Element 10 be divided into three piezoelectric segments comprised of a single Middle Segment (MS) 14 and two Outer Segments (OSs) 16. As represented, Middle Segment (MS) 14 is connected through a Circuit Lead 18 to a First Transmit/Receive Circuit (TRC) 20 to form the transmit/receive element of a first aperture and Outer Segments (OSs) 16 are interconnected by an Interconnect Lead 22 to form a single unit to together form the transmit/receive element of the second aperture, and are thereafter connected through a Circuit Lead 24 to a Second Transmit/Receive Circuit (TRC) 26. In alternate embodiments, Second Transmit/Receive Circuit (TRC) 26 may be replaced by a switch which selectively connects either Middle Segment (MS) 14 or the two Outer Segments (OSs) 16 to the single First Transmit/Receive Circuit (TRC) 20. It will be noted, as is well understood in the art, that all Elements 10 of the transducer are constructed and interconnected in the same manner as illustrated for the single Element 10 in FIG. 1A and that the Elements 10 will each have a connection to signal ground as indicated in FIG. 1A, usually as a common connection shared by all Elements 10.

Figure 1B:
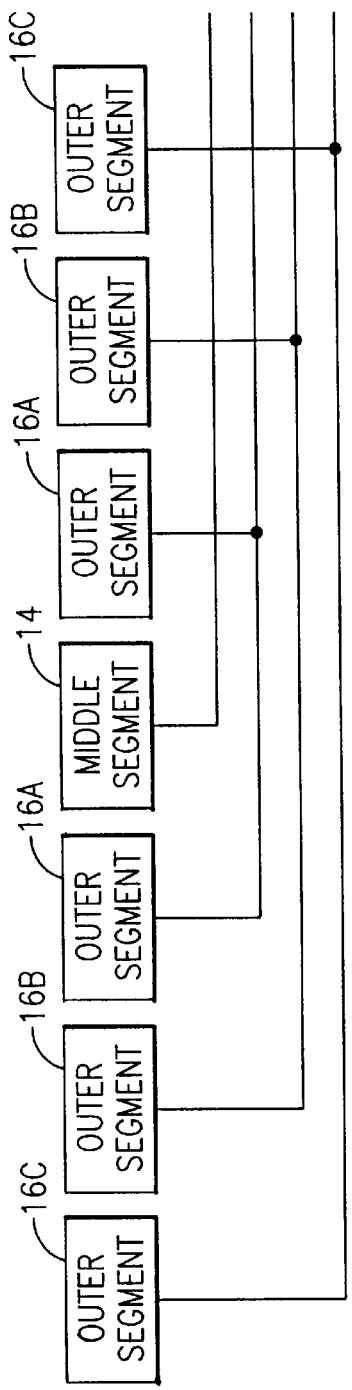
FIG. 1B is an illustration of the segments and connections of a four aperture transducer.

It will be recognized by those of ordinary skill in the arts that the element construction and segment connections and interconnections illustrated in FIG. 1A may be extended at will to transducers having larger numbers of apertures. For example, FIG. 1B illustrates a piezoelectric Element 10 of a four aperture transducer. In this transducer, Middle Segment (MS) 14 comprises the transmitting/receiving element for a first aperture, first Outer Segments (OSs) 16A are interconnected to form the transmit/receive element of a second aperture, second Outer Segments (OSs) 16B are interconnected to form the transmit/receive element of a third aperture, and third Outer Segments (OSs) 16C are interconnected to form the transmit/receive element of a fourth aperture. This construction may be expanded indefinitely, adding successive pairs of Outer Segments (OSs) 16 with the Middle Segment (MS) 14 forming one aperture and each successive pair of Outer Segments (OSs) 16 located symmetrically outwards from Middle Segment (MS) 14 forming additional apertures. Again, Middle Segment (MS) 14 and Outer Segments (OSs) 16 will further have a connection to ground.

Figure 2:
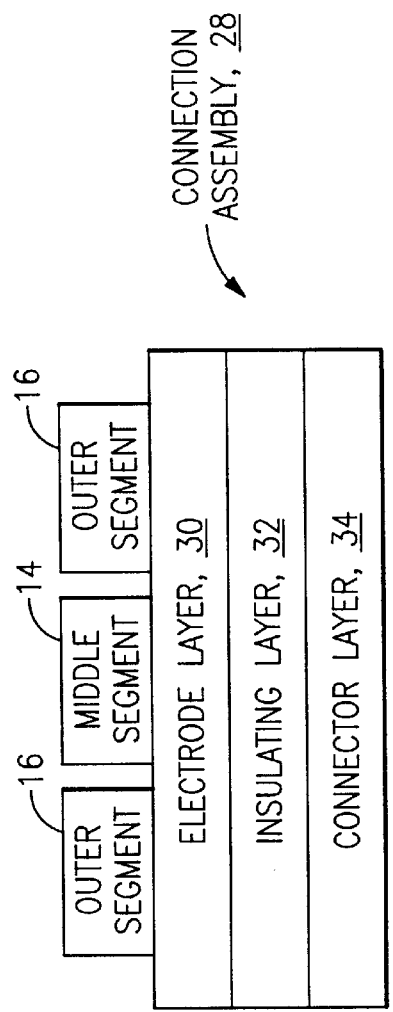
FIG. 2 is a cross sectional representation of a two aperture transducer.

As represented diagrammatically in the cross section of Transducer 12 illustrated in FIG. 2, the segment interconnections and connections of the present invention are formed in a multi-layered Connection Assembly 28 that is comprised of an Electrode Layer 30, an Insulating Layer 32 and a Connection Layer 34. It will be recognized by those of skill in the arts that, although Insulating Layer 32 and Connection Layer 34 are represented in FIG. 2 as single layers for simplicity and clarity of representation and discussion, Insulating Layer 32 and Connection Layer 34 may each or both be comprised of multiple layers and that the layers of Insulating Layer 32 and Connection Layer 34 may be interleaved as necessary to isolate Connection Layers 34 from one another and from Electrode Layer 30.

As will be described in further detail below, Electrode Layer 30 is a conductive layer typically comprised of gold with underlying layers of one or more other metals to promote adhesion and defines the electrode areas for the apertures, that is, the connections to the piezoelectric Segments 16 and 14 to form the transmit/receive elements of Transducer 12. Insulating Layer 32, in turn, may be comprised of such materials as polymide, silica, and a variety of other oxides, nitrides and polymers and selectively insulates areas of Electrode Layer 30 from Connection Layer 34. Connection Layer 34, in turn, is comprised of another layer of conductive metal or metals similar to Electrode Layer 30 and provides the necessary connections between the electrodes of Electrode Layer 30, that is, between the piezoelectric segments, to form the transmit/receive elements of the apertures, such as between two Outer Segments (OSs) 14A, and between the Middle Segment (MS) 16 and Outer Segments (OSs) 14 and the flex circuits connecting the piezoelectric segments to the Transmit/Receive Circuit (TRC)s 20, 26 and so on. As will be described below, Connection Assembly 28 has a total acoustic thickness of approximately 5 to 10 microns, and thereby does not adversely affect the acoustic characteristics of the transducer assembly.

Lastly, it will be noted that, as described above, Middle Segment (MS) 14 and Outer Segments (OSs) 16 will have connections to ground, often implemented as a common connection that is shared by all Segments 14,16 and that is connected to the faces of Segments 14,16 opposite the faces connecting to Electrode Layer 30. A common method for implementing this ground connection is through a ground plane that may be implemented, for example, as a layer on the faces of Segments 14,16 opposite Connection Assembly 28 with the ground layer extending to the edges of Elements 10 for connection to ground. Another method is a "wrap-around" electrode that makes contact with the faces of Elements 10 opposite Connection Assembly 28 and that wraps around the edges of Segments 14,16 to the edges of Segments 14,16 on the faces of Segments 14,16 adjacent Connection Assembly 28, thereafter making connection to an additional ground plane in Connection Assembly 28 by means of connections extending through "vias", or conductive passages, through Connection Assembly 28 and to the ground plane therein. It will be noted that these ground connections are not explicitly illustrated or shown in the following descriptions or the figures referred to therein, for purposes of clarity of presentation and discussion, but are present and, as well understood by those of ordinary skill in the relevant arts, may be implemented using the methods just discussed and other analogous methods.

The construction of Connection Assembly 28 with the three layers thereof is further illustrated in FIGS. 3A through 3F, which present a diagrammatic views of the segments of a two aperture Transducer 12 a viewed from the "bottom" or "back" side, that is, as viewed from the side of the piezoelectric transducer elements away from the transmitting and receiving side or surface of the transducer, with the layers and assembly of Connection Assembly 28. It will be understood that the components of Construction Assembly 28 as illustrated in FIGS. 3A through 3F and in the following text illustrate the structure and construction of each component thereof in the area of and under a single Element 10 of the exemplary Transducer 12 and that this structure and construction will be repeated as a single continuous structure extending under each Element 10 of the Transducer 12 and for the entire length of the linear array comprised of the Elements 10.

As illustrated in FIGS. 3A and 3B wherein FIG. 3A shows Electrode Layer 30 and FIG. 3B the assembly of Electrode Layer 30 to the segments of an Element 10 of the Transducer 12, Electrode Layer 30 is comprised of an Electrode Area (EA) 36 for and corresponding to each piezoelectric segment of the Element 10. Electrode Layer 30 thereby includes, in the present example, a Middle Electrode Area (EA) 36 for and corresponding to Middle Segment (MS) 14 and two Outer Electrode Areas (EAs) 38, each for and corresponding to one of Outer Segments (OSs) 16. It will be noted that, as indicated, the edge or edges of at least one of Outer Electrode Areas (EAs) 38 adjacent an edge of the Element 10, that is, the edge or edges of at least one of Outer Electrode Areas (EAs) 38 furthest away from Middle Segment (MS) 14, may extend outwards past the outer edge of the Outer Segment (OS) 16 to provide an area in which to attach a flex circuit to the Outer Electrode Area (EA) 38 as will be described below, the flex circuit then leading to the Transmit/Receive Circuits (TRCs) 20, 26.

The extension of Electrode Layer 30 for other transducers having greater numbers of apertures, that is, greater numbers of piezoelectric segments, will be apparent to those of ordinary skill in the art without further discussion. For example, there will again be a Middle Electrode Area (EA) 36 connecting to a Middle Segment (MS) 14 forming a first aperture of the Transducer 12 and a pair of Outer Electrode Areas (EAs) 38 connecting to a corresponding pair of Outer Segments (OSs) 16 symmetrically located on either side of Middle Segment (MS) 14 for, and forming, each additional aperture.

Electrode Layer 30 is generally constructed as a single piece using standard photolithographic techniques, with the breaks between Middle Electrode Area 36 and Outer Electrode Areas 38 being defined by standard photolithographic lift-off or etching processes. Electrode Layer 30 would typically have a thickness in the range of about 0.05 microns to 2.0 microns, depending upon the material and voltages, while Middle Segment (MS) 14 and Outer Segments (OSs) 16 would typically have dimensions in the range of 0.1 mm to 20 mm in medical devices and the breaks between Middle Segment (MS) 14 and Outer Segments (OSs) 16 would typically be in the range of 10 microns to 100 microns.

Referring now to FIGS. 3C and 3D, FIG. 3C illustrates Insulating Layer 32 for the two aperture Transducer 12 of the present example, while FIG. 3D illustrates the assembly of Insulating Layer 32 to the segments of the Element 10 and to the preceding Electrode Layer 30. As illustrated therein, Insulating Layer 32 effectively extends over the entire area of one of Outer Segments (OSs) 16 with a Segment-to-Segment Connection Opening (SSCO) 40 therethrough in the area of that Outer Segment (OS) 16 and has an Outer Segment-to-Segment Connection Area (SSCA) 42 extending from the area of Segment-to-Segment Connection Opening (SSCA) 40 and across Middle Segment (MS) 14 and to and extending over a part of the other Outer Segment (OS) 16. Insulating Layer 32 further has a Middle Segment (MS) Connection Opening (MSCO) 44 therethrough in the area of Middle Segment (MS) 14 and a Middle Segment (MS) Connection Area (MSCA) 46 extending from Middle Segment (MS) 14 and across one of Outer Segments (OSs) 16 and to and past the outer edge of that Outer Segment (OS) 16, in this example across the Outer Segment (OS) 16 that is associated with Segment-to-Segment Connection Opening (SSCO) 40. As illustrated, Middle Segment Connection Opening (MSCO) 44 is offset laterally from Outer Segment-to-Segment Connection Area (SSCA) 42 so that a connecting lead may be run from Segment-to-Segment Connection Opening (SSCO) 40 and across Outer Segment-to-Segment Connection Area (SSCA) 42 to the other Outer Segment (OS) 16 without the connecting lead passing over or too near Middle Segment Connection Opening (MSCO) 44, thereby avoiding a possible accidental short circuit.

The extension of Insulating Layer 32 to transducers having greater than two apertures will again be well understood by those of ordinary skill in the arts. For example, there will be a Segment-to-Segment Connection Opening (SSCO) 40 and a corresponding Outer Segment-to-Segment Connection Area (SSCA) 42 for and corresponding to each pair of Outer Segments (OSs) 16 forming an aperture, although at least some of the Outer Segment-to-Segment Connection Areas (SSCAS) 42 may have a Segment-to-Segment Connection Opening (SSCO) 40 at each end rather than simply terminating at the other Outer Segment (OS) 16. In addition, there will be a Middle Segment Connection Opening (MSCO) 44 in the area of Middle Segment (MS) 14 and a corresponding Middle Segment Connection Area (MSCA) 46, and connections to the flex circuit connections between the segments and Transmit/Receive Circuit (TRC)s 20, 26.

The typical relative dimensions of Insulating Layer 32 may be determined from the above typical dimensions given for Electrode Layer 30 and the segments of the Element 10, and Insulating Layer 32 will have a thickness dependent upon the material chosen and the maximum voltage to be applied and may typically be in the range of 0.5 microns to 20 microns.

Referring finally to FIGS. 3E and 3F, FIG. 3E illustrates Connection Layer 34 for the two aperture Transducer 12 of the present example, while FIG. 3F illustrates the assembly of Connection Layer 34 to the segments of the Element 10 and to the preceding Electrode Layer 30 and Insulating Layer 32. As illustrated therein, Connection Layer 34 of the present example includes an Outer Segment-to-Segment Connector (OSSC) 48 extending from the area of Segment-to-Segment Connection Opening (SSCO) 40 and across Outer Segment-to-Segment Connection Area (SSCA) 42 to interconnect the two Outer Segments (OSs) 16 through the corresponding Outer Electrode Areas (EAs) 38. Connection Layer 34 also has a Middle Segment Connector (MSC) 50 extending from Middle Segment Connection Opening (MSCO) 44 and across Middle Segment Connection Area (MSCA) 46 to connect Middle Segment (MS) 14 to the flex circuits through Flex Contact Area (FCA) 52 of Middle Segment Connector (MSC) 50.

Finally, it will be noted that Outer Segments (OSs) 16 are connected to the flex circuits at a Flex Contact Area (FCA) 54 located in one of Outer Electrode Areas (EAs) 38, with Flex Contact Area (FCA) 54 being shown in the present example as located in the Outer Electrode Area (EA) 38 not occupied by Segment-to-Segment Connection Opening (SSCO) 40. It will be understood to be functionally equivalent, however, if Outer Segment-to-Segment Connection Area (OSCA) 42 and Outer Segment-to-Segment Connector (OSSC) 48 continue to the edge of the Element 10 to form a Flex Contact Area (FCA) 54 of or on the Outer Segment-to-Segment Connector (OSSC) 48 rather than on the Outer Electrode Area (EA) 38, in a manner similar to how Flex Contact Area (FCA) 52 is constructed and connected for Middle Segment Connector (MSC) 50.

Again, the extension of Connection Layer 34 to transducers having greater than two apertures will be well understood by those of ordinary skill in the arts. For example, there will be a Middle Segment Connector 50 extending from Middle Segment Connection Opening 44 and across Middle Segment Connection Area 46 to connect Middle Segment (MS) 14 to the flex circuits through Flex Contact Area 52 of Middle Segment Connector 50. There will also be, for each pair of Outer Segments (OSs) 16 forming an aperture, an Outer Segment-to-Segment Connector 48 extending from the corresponding Segment-to-Segment Connection Opening 40 and across Outer Segment-to-Segment Connection Area 42 to interconnect the two Outer Segments (OSs) 16 of the aperture through their corresponding Outer Electrode Areas 38. In addition, the Outer Segment-to-Segment Connector 48 of each pair of Outer Segments (OSs) 16 forming an aperture will extend onwards toward one edge of the Element 10 and to a corresponding Flex Contact Area 54 formed at the edge of the Element 10, with Insulating Layer 32 being correspondingly extended to provide an insulating layer between the Outer Segment-to-Segment Connectors 48 and the Electrode Areas 36 and 38 crossed by the Outer Segment-to-Segment Connectors 48.

Again, the typical dimensions of the various conductor paths of Connection Layer 34 may be determined from the typical dimensions given previously for Elements 10, Electrode Layer 30 and Insulating Layer 32 and the number of apertures provided by the transducer, which in turn determines the number of Outer Segment-to-Segment Connectors 48. In addition, it will be noted that these conductor paths will typically have a minimum width and a spacing that are determined by photolithographic capabilities and conceivably may be less than 0.5 microns, but will more likely be in the range of 1 micron to 10 microns. In practice, the paths will be made as wide as possible in the given space without causing shorts between paths.

Finally, it will be apparent that the design and construction of a multiple aperture transducer as shown in FIGS. 3A through 3F and as discussed above is exemplary and that other arrangements of transducer segments, electrode areas, Insulating Layer or Layers 32 and Connection Layer or Layers 34 are possible and fall within the design and construction principles described herein above. For example, a given Element 10 need not be constructed with an odd number of Segments 14,16 but may be constructed and connected as described above with an even number of segments, effectively deleting Segment 14 from the structure. Also, the arrangement and dimensions of the Segments 14, 16 and the corresponding layouts of Insulating Layer or Layers 32 and Connection Layer or Layers 34 need not be symmetric, either about the longitudinal center line of the array or with respect to one another. Again, it will be recognized by those of skill in the arts that, although Insulating Layer 32 and Connection Layer 34 are represented in FIGS. 3A through 3F as single layers for simplicity and clarity of representation and discussion, Insulating Layer 32 and Connection Layer 34 may each or both be comprised of multiple layers and that the layers of Insulating Layer 32 and Connection Layer 34 may be interleaved as necessary to isolate Connection Layers 34 from one another and from Electrode Layer 30.

B. Multi-Layer Backplane Interconnections for Multiple Segment and Multiple Element Transducers With Reduced Cross-Overs The above discussions have described the construction and method of construction of multiple segment transducers having interconnections between and connections to the segments of the transducer through a multi-layer backplane. This technique may also be used for other types of transducers and, in particular, all forms of linear or curved linear array transducers wherein each piezoelectric Element 10 of the transducer is comprised of multiple piezoelectric sub-elements that are mechanically distinct but are electrically connected to operate as single, larger elements. For example, in many linear and curved linear arrays, the element pitch is sufficiently large that the individual Elements 10 are longitudinally diced into smaller sub-elements for acoustic reasons. This may be illustrated with the aid of FIG. 4A, which is similar to FIG. 1B except that each Element 10 is longitudinally sliced into two or more Sub-Elements 56 wherein each Sub-Element 56 extends across the width of the face of the Transducer 12 and includes a Middle Segment (MS) 14 and corresponding Outer Segments (OSs) 16. Each of these sub-elements then requires a pattern of interconnections as described above, and each aperture segment of such an individual sub-element must be electrically connected to other aperture segments.

When building transducers having more than two apertures, or when building transducers comprised of sub-elements as described just above, the connections to and interconnections between the segments and sub-elements generally requires the use of flex circuits, or equivalent forms of circuits, to form certain of the interconnections between the segments or sub-elements. These flex circuits, or other equivalent forms of circuits, in turn frequently require electrical cross-over paths in order to make the necessary interconnections, that is, electrical paths which must be kept electrically isolated from one another but which physically cross over one another. Cross-overs, however, significantly increase the cost of construction of the transducer and require additional space in areas where the additional space is either generally not available or desired. While the use of cross-overs in flex circuits can be avoided by the user of multiple flex circuits, or the equivalent, this again increases the cost, complexity and bulk of the transducer unit and is likewise undesirable and is generally impractical for curved linear arrays.

Figure 4A:
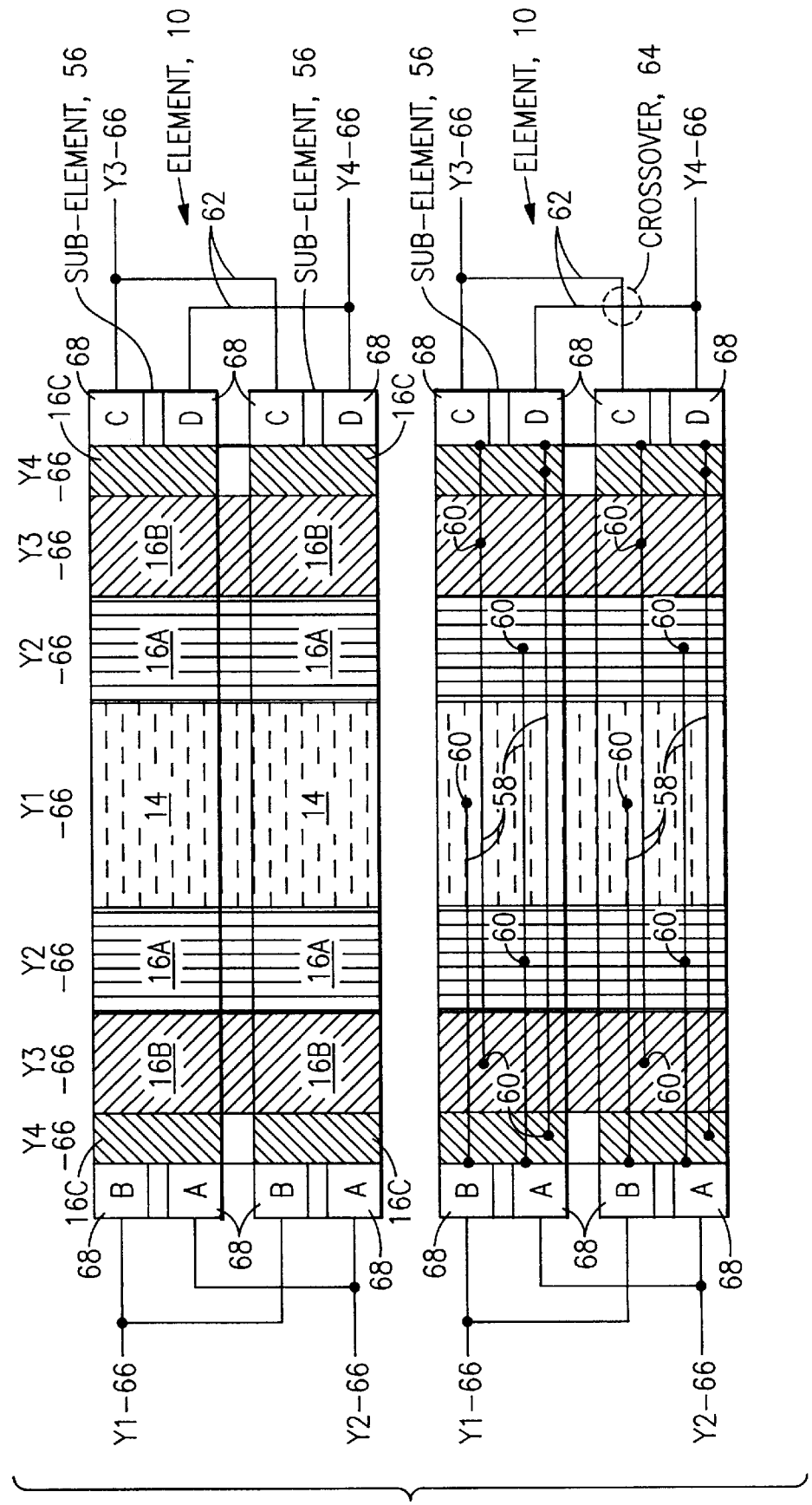
FIGS. 4A and 4B are diagrammatic representations of Y-Group layouts and connections.

This problem may be again illustrated with the aid of FIG. 4A, which illustrates the connections and interconnections required for a four aperture transducer with Sub-Elements 56. FIG. 4A shows the interconnection and connections for a single pair of Sub-Elements 56 with an adjacent pair of Sub-Elements 56 indicated in outline form. The connections of and between Middle Segments (MSs) 14 and Outer Segments (OSs) 16 and between the Sub-Elements 56 are shown for a pair of Sub-Elements 56, wherein the Segment-to-Segment Connections 58 formed, for example, by Connection Layer 34, are indicated by lines therein with the Connections 60 to the Segments 14, 16 indicated by squares. The Sub-Element Connections 62 between the Sub-Elements 56, for example, by flex circuits, are shown at the edges of the Sub-Elements 56 with an exemplary Cross-Over 64 explicitly indicated and other Cross-Overs 64 shown. In FIG. 4A, and in FIG. 4B, those segments of each Sub-Element 56 that are connected together electrically to form corresponding apertures are indicated by shading of the segments, similar shading indicating an electrical connection into a single unit.

As may be seen from FIG. 4A, each pair of Outer Segments (OSs) 16 located symmetrically to either side of Middle Segment (MS) 14 are connected by a thin film interconnected as described above, and each such connected pair is referred to as a "Y-group", indicated in FIG. 5B as Y-Groups Y1-66 through Y4-66. In each Sub-Element 56, the connection for each part of each aperture is brought out to one of Pads 68A through 68D, which are interconnected, as shown, by flex circuits, resulting in Cross-Overs 64. Cross-Overs 64 would then have to be implemented either with "vias", that is, pass-through conductors, in the flex circuits or by using multiple flex circuits for the interconnections.

Figure 4B:
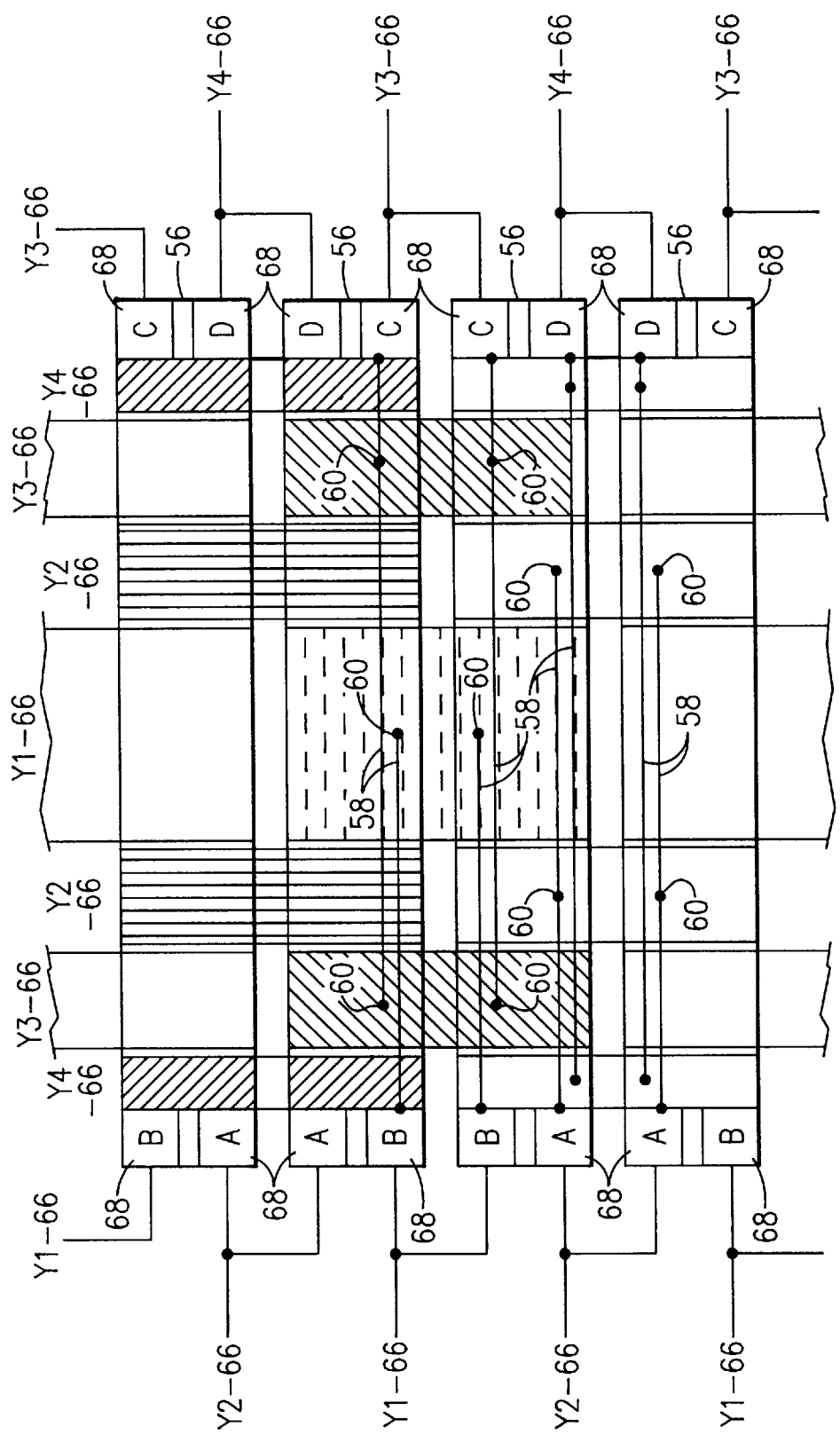

The interconnection method and construction of the present invention is illustrated in FIG. 4B wherein the Sub-Elements 56 of FIG. 4B correspond generally to those shown in FIG. 4A. As illustrated therein, Sub-Elements 56 are now grouped according to the connections between Y-Groups 66, with half of the aperture Segments 14,16 of a given Sub-Element 56 of FIG. 4B now being offset along the length of the array of Sub-Elements 56 by one Sub-Element 56, that is, shifted along the transducer array by one Sub-Element 56, relative to the other half of the aperture Segments 14,16 of the Sub-Element 56 of FIG. 4B, and the order of Pads 68 are now reversed on every other Sub-Element 56. As illustrated in FIG. 4B, the flex circuit leads can now interconnect the Y-Groups 66 in a manner that requires no Cross-Overs 64 to connect adjacent Sub-Elements 56.

It should be noted that this method of interconnection is most advantageous in transducers wherein there are two sub-elements in each major element of the transducer. For example, this connection method will still require cross-overs when implemented in transducers using three sub-elements in each major elements, but the method of the present invention will eliminate one half of the cross-overs, thereby significantly reducing the cost and complexity of the transducers. Also, the method of the present invention as described just above is less advantageous in transducers having more than four Y-groups, but the number of cross-overs required would again be significantly reduced. Still other transducers generally will not require or will not benefit as significantly from the connection method described just above. Examples would include transducers with monolithic elements, that is, transducers wherein the elements are not longitudinally diced into two or more sub-elements as no cross-overs would be required in any case. Yet another example is expanding aperture transducers wherein the benefit of the interconnection method described just above is reduced as the Y-groups of a single element are either connected or not connected to a single transmitter/receiver circuit. The effective element shape thereby becomes somewhat "kinked", which may increase the effective element width somewhat, but is of little consequence as such simple expanding aperture transducers offer little benefit beyond two aperture sizes, which can be connected without any cross-overs.

Finally, it will be apparent that the design and construction of a multiple aperture transducer as shown in FIGS. 4A and 4B and as discussed above is exemplary and that other arrangements of transducer segments and sub-elements and electrode areas, and of the Insulating Layer or Layers 32 and Connection Layer or Layers 34 as were illustrated previously with reference to FIG. 2, are possible and fall within the design and construction principles described herein above. For example, a given element need not be constructed with an odd number of segments or sub-elements but may be constructed and connected as described above with an even number of segments or sub-elements. Also, the arrangement and dimensions of the segments or sub-elements and the corresponding layouts of Insulating Layer or Layers 32 and Connection Layer or Layers 34 need not be symmetric, either about the longitudinal center line of the array or with respect to one another. Again, it will be recognized by those of skill in the arts that, although Insulating Layer 32 and Connection Layer 34 as may be used in the construction discussed with reference to FIGS. 4A and 4B are represented in FIG. 2 as single layers for simplicity and clarity of representation and discussion, Insulating Layer 32 and Connection Layer 34 may each or both be comprised of multiple layers and that the layers of Insulating Layer 32 and Connection Layer 34 may be interleaved as necessary to isolate Connection Layers 34 from one another and from the electrodes.

C. Deposition Construction of Multi-Layer Backplane Interconnections

The above discussions have described the multiple layers of the backplane transducer segment interconnections as having been formed by standard photolithographic processing techniques. Such techniques, however, are sometimes not suitable for use with certain piezoelectric materials for chemical, thermal, mechanical or logistical reasons and it is therefore sometimes preferable to use alternate techniques to manufacture the transducer backplane interconnections, such as the deposition techniques that are also generally well known in the art.

In this method, which is illustrated in FIGS. 5A through 5C and FIGS. 6A and 6B, the Electrode Layer 30 is deposited on the back, that is, the backing body side, of the piezoelectric material, which at this point is a monolithic body of material, and the breaks between Middle Segment (MS) 14 and Outer Segments (OSs) 16 are defined photolithographically or, alternatively, by laser ablation, mechanical scribing, or an equivalent technique. Insulating Layer 32 and Connection Layer 34 are then deposited in reverse order on a Carrier 70, that is, Connection Layer 34 is deposited on Carrier 70 and Insulating Layer 32 is deposited over Connection Layer 34, wherein Carrier 70 is comprised of silicon, glass or other equivalent and convenient material. Carrier 70 with Insulating Layer 32 and Connection Layer 34 are then attached to the back side of the piezoelectric material, that is, onto the side of the piezoelectric material bearing Electrode Layer 30 and in alignment with Electrode Layer 30, using a thin line glue bond, low temperature solder, or similar method of attachment. It should be noted that this step requires that Insulating Layer 32 cover generally all of Electrode Layer 30, except for the vias necessary for the actual electrical connections between Electrode Layer 30 and Connection Layer 34 and any other connections, so that the surfaces to be bonded are planar.

After bonding Carrier 70 with Insulating Layer 32 and Connection 34 to the piezoelectric material bearing Electrode Layer 30, Carrier 70 may be removed by mechanical grinding, chemical etching or a combination of such methods, and the resulting assembly attached to a Backing Body 72, as illustrated in FIG. 6A. Alternately, and as illustrated in FIG. 6B, all or part of Carrier 70 may be left to comprise part of the acoustic and mechanical structure on which the Transducer 12 is mounted and, in this instance, the flex circuit connections could be made on the metal areas of Carrier 70 rather than directly to the areas on Electrode Layer 30.

In an alternate method of construction, Electrode Layer 30 is deposited on the back, that is, the backing body side, of the piezoelectric material, which at this point is a monolithic body of material, and the breaks between Middle Segment (IS) 14 and Outer Segments (OSs) 16 are defined photolithographically or, alternatively, by laser ablation, mechanical scribing, or an equivalent technique. Insulating Layer 32 and Connection Layer 34 are then deposited directly onto the back side of the piezoelectric material, that is, directly onto Electrode Layer 30. A Carrier 70 or equivalent backing body may then be bonded to the Connection Assembly 28, in the manner described above, and the block of piezoelectric material is then diced to form the individual elements. This method has the advantage over the method described just above that the method does not require precise registration between a Carrier 70 with an Insulating Layer 32 and Connection Layer 34 and a block of piezoelectric material bearing the Electrode Layer 30 during assembly and avoids the use of a mechanical bond between the Electrode Layer 30 and the Insulating Layer 32 and Connection Layer 34.

It will be noted that these methods of construction offers several advantages over the methods of the prior art. For example, these methods use a minimum number of flex circuit connections to the piezoelectric material, resulting in increased reliability and fewer alignment problems and lower costs. In addition, no connections are required to the central portions of the piezoelectric material, resulting in easier manufacture, particularly for curved linear arrays, and no external interconnections are required for electrically common aperture segments.

Further, the structure comprising the electrical connections to the piezoelectric material can be made thin enough to be acoustically inconsequential, and the resulting resolution capabilities of transducers made in this manner allows the manufacture of transducers having operating frequencies up to at least 10 MHz.

Finally, this method can be adapted to transducers comprised of multiple piezoelectric layers, it places few constraints on materials and construction methods used in other steps in manufacturing transducers, and it can be adapted for use in routing the bias voltages used to control multi-aperture electrostrictive transducers.

Again, it will be apparent that the design and construction of a multiple aperture transducer as discussed above is exemplary and that other arrangements of transducer segments, sub-elements, electrode areas, and insulating and connection layers, are possible and fall within the design and construction principles described herein above. For example, a given element need not be constructed with an odd number of segments or sub-elements but may be constructed and connected as described above with an even number of segments or sub-elements. Also, the arrangement and dimensions of the segments or sub-elements and the corresponding layouts of the insulating and connection layers need not be symmetric, either about the longitudinal center line of the array or with respect to one another. Again, it will be recognized by those of skill in the arts that the insulating and connection layers may each or both be comprised of multiple layers and that the layers of insulating and connection layers may be interleaved as necessary to isolate the connections from one another and from the electrodes.

D. Multi-Layer Backplane Interconnections With An Electrode Layer Substrate

The method for constructing a transducer Connection Assembly 28 described Electrode Layer 30 as deposited directly on the back of the piezoelectric material with Insulating Layer 32 and Connection Layer 34 deposited on a Carrier 70 and then superimposed on Electrode Layer 30. It is recognized, however, that this method may not be an optimum approach in certain instances. For example, placing Electrode Layer 30 directly on the piezoelectric material increases the cost of this component of the transducer due to the cost of the thin film disposition process combined with the brittle nature of the piezoelectric material and the thereby potentially low yield of this manufacturing process. If Electrode Layer 30 is placed on a separate component of the assembly, however, such as on Carrier 70 as a deposited layer with Insulating Layer 32 and Connection Layer 34, the component bearing Electrode Layer 30 must be carefully chosen to avoid degradation of transducer performance due to its acoustic characteristics and effects.

Further, if Electrode Layer 30 and Carrier 70 with Insulating Layer 32 and Connection Layer 34 is placed on the back of the piezoelectric material, in the manner described above, then the ends of the piezoelectric material may have to extend over the edges of Backing Body 72 to allow connections to Electrode Layer 30. As a consequence, the edges of the piezoelectric material may not be properly damped by Backing Body 72, thereby degrading the performance of the transducer, and, although additional backing may be added to Backing Body 72 in these areas to provide the necessary damping, this is an additional manufacturing step with additional cost.

Finally, it will be noted that many if not most transducers are provided with a matching layer on their front face, that is, the radiating and receiving face that faces away from Backing Body 72. If, however, Electrode Layer 30, Insulating Layer 32 and Connection Layer 34 are deposited on the front face of the piezoelectric material to avoid the above problem, the edges of the piezoelectric material may either thereby not have a satisfactory matching layer on their radiating and receiving face, again degrading the performance of the transducer, or the provision of a satisfactory matching layer becomes more difficult.

Figure 7:
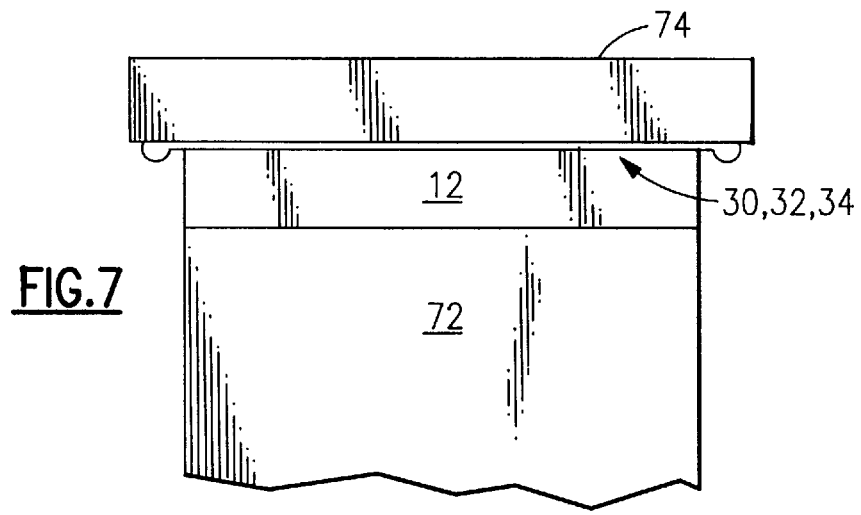
FIG. 7. is a side view of a transducer with a carrier as a matching layer.

A solution to this problem is illustrated in FIG. 7, wherein it is shown that Electrode Layer 30, Insulating Layer 32 and Connection Layer 34 are deposited as thin films on a Matching Layer Carrier 74 wherein Matching Layer Carrier 74 is a substrate comprised of a material such as glass or crystalline material that has been chosen to have the appropriate acoustic impedance and thickness to function as a matching layer for the transmitting and receiving face of the Transducer 12.

This method is advantageous in that glass, crystalline material and similar materials are "tougher" and less brittle than piezoelectric materials and are available as standard thin film substrates, thereby lowering the cost of manufacture and increasing the production yield and reliability of the component. In addition, placing Electrode Layer 30 on a Matching Layer Carrier 74 rather than on the piezoelectric material allows more flexibility in choosing the piezoelectric material as the piezoelectric material now does not have to be compatible with thin film deposition techniques.

Finally, material such as glass and crystalline material inherently have acoustic impedances to act as matching layer materials, thereby gaining two functions from a single component, and such materials are not piezoelectrically active, so that a small extension of the material past the edge of Backing Body 72 generally does not adversely affect the performance of the transducer.

Again, it will be apparent that the design and construction of a multiple aperture transducer as discussed above is exemplary and that other arrangements of transducer segments, sub-elements, electrode areas, and insulating and connection layers, are possible and fall within the design and construction principles described herein above. For example, a given element need not be constructed with an odd number of segments or sub-elements but may be constructed and connected as described above with an even number of segments or sub-elements. Also, the arrangement and dimensions of the segments or sub-elements and the corresponding layouts of the insulating and connection layers need not be symmetric, either about the longitudinal center line of the array or with respect to one another. Again, it will be recognized by those of skill in the arts that the insulating and connection layers may each or both be comprised of multiple layers and that the layers of insulating and connection layers may be interleaved as necessary to isolate the connections from one another and from the electrodes.

E. Via and Connection Structures for Multiple Elevation Transducers

The problems encountered in constructing multiple elevation transducers have been discussed in detail above and, in brief, are essentially one of providing a connection structure that allows the Middle Segments (MSs) 14 of a Transducer 12 and the Outer Segments (OSs) 16 not directly adjacent the edges of the Transducer 12 to be brought out to the edge of the Transducer 12 for connection to the flex circuits in the minimum width and minimum thickness and with the least complexity.

As has been described, a connection to each Segment 14 or 16 in each Element 10 or Sub-Element 56 must be run from the segment to another segment or from the segment to the edge of the array within the width of the Element 10 or Sub-Element 56 segment. The horizontal space required for the connections thereby limits both the number of Elements 10 or Sub-Elements 56 that can be constructed per unit length along the length of the array and the number of Segments 14,16 that can be constructed across the width of the array in each Element 10 or Sub-Element 56, thereby limiting the resolution of the array. The connections must also be made in a manner that occupies the minimum thickness relative to the acoustic dimensions of the transducer because of possible adverse effects upon the acoustic characteristics of the transducer.

In this regard, it should be noted that the Elements 10 or Sub-Elements 56 of many transducers are not constructed out of single layers of piezoelectric material, as in the exemplary transducers discussed above, but, for acoustic and mechanical reasons, are constructed from multiple layers of piezoelectric material. The above problems are thereby compounded in that each Segment 14,16 of each Element 10 or Sub-Element 56 may thereby not be a single piece of piezoelectric material requiring a single signal connection and a single ground connection to each other segment or leading to the edge of the array, but may be comprised of multiple pieces of piezoelectric material, each of which requires ground and signal connections.

Finally, any technique used to construct the connections between segments and from the segments to the flex circuits must also be adaptable to the preferred methods for constructing transducers. As has been described above, in the preferred construction one or more pieces of piezoelectric material, each comprising a layer of the piezoelectric material for all of the Elements 10 or Sub-Elements 56 of the transducer, are assembled with one or more circuit and insulating layers comprising the signal and ground connections for all of the Elements 10 or Sub-Elements 56 of the transducer. The resulting assembly of piezoelectric material and connection circuits is then diced, that is, sliced with a saw, laser, scribing or similar method, along the boundaries between each Element 10 or Sub-Element 56 and along the boundaries between the Segments 14, 16, mounted on a Backing Body 72, and connected to the flex circuits and cables connecting to the transmit/receive circuits.

The present invention additionally provides methods for the construction of multiple aperture transducers, including multiple aperture transducers having multiple planes of piezoelectric material, that requires less horizontal and vertical space for the connection and interconnection of the segments thereof As will be described in detail below, these methods include staggering the connections leading between Middle Segments (MSs) 14 and the edges of the Transducer 12 with each successive Element 10 or Sub-Element 56 so that the successive connections between Middle Segments (MSs) 14 and the edges of Elements 10 or Sub-Elements 56 are to opposite sides of the Transducer 12. The width of each Element 10 or Sub-Element 56 must therefore accommodate only a single connection between the Middle Segment (MS) 14 and the edge of the Element 10 or Sub-Element 56.

These methods further include the connection construction wherein the connections leading from Middle Segment (MS) 14 and Outer Segments (OSs) 16 to the edge of the array and between the Outer Segments (OSs) 16 of an Element 10 or Sub-Element 56 are brought to a portion of Connection Layer 34 that is below or outside the dicing cuts so that the connections provided in that portion of Connection Layer 34 are not cut during the dicing operation. This method is particularly useful in transducers wherein each Element 10 is diced into two or more Sub-Elements 56 as each group of Sub-Elements 56 in each Element 10 that together comprise a Segment 14,16 or an aperture remain connected into a single electrical unit by the connections in the uncut portion of Connection Layer 34. As a result, each group of Sub-Elements 56 of an Element 10 that together comprise a Segment 14,16 or an aperture requires only a single connection at the edge of the array, rather than a connection for each individual Sub-Element 56.

Finally, it has been described above and will be described further in the following that the connections between the piezoelectric segments and the connections of Connection Layer 34 and connections between the piezoelectric segments themselves require the use of vias, that is, conductive pathways or connections leading between the layers of piezoelectric material and the layers of Connection Assembly 28. The present invention includes the method for placing vias in the layers in a staggered manner in the middle areas of the Elements 10 or Sub-Elements 56 so that the necessary via connections will remain intact after the dicing process regardless of the alignment between the dicing lines and the vias. The present invention also includes the method for placing the vias in the layers outside or below the dicing lines along the outer areas of the array so that, again, the necessary via connections will remain intact after the dicing process regardless of the alignment between the dicing lines and the vias.

1. Alternating Routing of Middle Segment Leads

Illustrating each of these methods in turn, various connector constructions using the method of alternating leads from Middle Segments (MSs) 14 to the left and right edges of two aperture linear Transducer 12 array are shown in diagrammatic form in the cross sectional views of an Element 10 in FIGS. 8A through 8D. FIG. 8A illustrates an embodiment using a single layer of piezoelectric material for each of Segments 14, 16 while FIGS. 8B through 9D illustrate embodiments using two layers of piezoelectric material for each of Segments 14,16.

As illustrated in FIG. 8A, an Element 10 is comprised of a single layer of piezoelectric material diced into a Middle Segment (MS) 14 and two Outer Segments (OSs) 16 which will be referred to hereafter as left Outer Segment (OS) 16L and right Outer Segment (OS) 16R, referring to their locations in FIG. 8A relative to Middle Segment (MS) 14. As represented therein, a Ground Plane 76 is imposed upon and connects to the upper face of Middle Segment (MS) 14 and Outer Segments (OSs) 16L and 16R. As has been discussed previously, and although not shown explicitly in FIG. 8A for simplicity of representation, Ground Plane 76 will normally wrap over the outer edge of one or both of Outer Segments (OSs) 16L or 16R and would attach to a flex circuit conductor to ground.

In addition, there are Outer Segment Conductors (OSCs) 78, identified respectively as Outer Segment Conductors (OSCs) 78L and 78R, located between the upper face of Backing Body 72 and, respectively, the bottom faces of Outer Segments (OSs) 16L and 16R. As shown, Outer Segment Conductor (OSC) 78L connects to the bottom face of Outer Segment (OS) 16L, that is, the face opposite Ground Plane 76, and runs to the left side of the array to connect to a corresponding conductor of a flex circuit. Likewise, Outer Segment Conductor (OSC) 78R connects to the bottom face of Outer Segment (OS) 16R, that is, the face opposite Ground Plane 76, and runs to the right side of the array to connect to a corresponding conductor of a flex circuit.

Finally, there is a Middle Segment Conductor (MSC) 80 located between Element 10 and Backing Body 72 that connects to the bottom face of Middle Segment (MS) 14 and runs under one of Outer Segments (OSs) 16L or 16R and its corresponding Outer Segment Conductor (OSC) 78 to connect to a conductor of the flex circuit on that side of the array. As has been briefly described above, the Middle Segment Conductors (MSCs) 80 of successive Elements 10 along the array run alternately to the left and right sides of the Elements 10, so that for each Element 10 there is an Outer Segment Conductor (OSC) 78 and the Middle Segment Conductor (MSC) 80 running to one edge of the Element 10 and the single remaining Outer Segment Conductor (OSC) 78 running to the other edge of the Element 10.

The expansion of this scheme to transducers having greater numbers of apertures and a greater number of symmetric pairs of Outer Segments (OSs) 16 will be apparent to those of ordinary skill in the arts. That is, the Outer Segment Conductors (OSCs) 78 for the Outer Segments (OSs) 16 one each side of Middle Segment (MS) 14 will run to their corresponding edge of the Element 10 and the additional Middle Segment Conductor (MSC) 80 of each Element 10 along the array will run alternately to one side and then the other of successive Elements 10. As such, the greatest number of conductors on either side of a given element will be equal to the number of pairs of Outer Segments (OSs) 16 plus a conductor for the Middle Segment (MS) 14 and thus will be equal to but no greater than the number of apertures of the transducer.

One implementation of this scheme for a two aperture transducer wherein each Middle Segment (MS) 14 and Outer Segment (OS) 16 of each Element 10 is comprised of two layers of piezoelectric material is illustrated in FIG. 8B. As shown therein, Middle Segment (MS) 14 is now comprised of an upper Middle Segment (MS) 14U and a bottom Middle Segment (MS) 14B while Outer Segments (OSs) 16 are now comprised of left upper, left bottom, right upper and right bottom Outer Segments (OSs) 16LU, 16LB, 16RU and 16RB.

In this implementation the signal conductors run between the layers of piezoelectric material while the ground planes run on either outer face of the sandwich of piezoelectric material and conductors. Thus, there is an Upper Ground Plane 76U on and connecting to the upper faces of Middle Segment (MS) 14U and Outer Segments (OSs) 16LU and 16RU and with a connection means wrapping over the outer edge of one or both of Outer Segments (OSs) 16LU or 16RU to attach to a flex circuit conductor to ground, and a Bottom Ground Plane 76B on and connecting to the lower faces of Middle Segment (MS) 14B and Outer Segments (OSs) 16LB and to the flex circuits ground. Referring to the space between the piezoelectric layers, it may be seen that there are upper right, bottom right, upper left and bottom left Outer Segment Conductors (OSCs) 78RU, 78BR, 78LU and 78LB connecting to, respectively, the lower face of Outer Segment (OS) 16RU, the upper face of Outer Segment (OS) 16RB, the lower face of Outer Segment (OS) 16LU and the upper face of Outer Segment (OS) 16LB and wrapping over the outer edges of Outer Segments (OSs) 16RB and 16LB to connect to the flex circuits.

Finally, there is a Middle Segment Conductor (MSC) 80 running between Middle Segments (MSs) 14U and 14B and connected to the lower face of Middle Segment (MS) 14U and the upper face of Middle Segment (MS) 14B and running between either Outer Segment Conductors (OSCs) 78RU and 78RB or Outer Segment Conductors (OSCs) 78LU and 78LB to wrap over the outer edge of one of Outer Segments (OSs) 16RB or 16LB to connect to a flex circuit conductor. As in the example of FIG. 8A, the Middle Segment Conductors (MSCs) 80 of successive Elements 10 along the array run alternately to the left and right sides of the Elements 10.

Referring to FIG. 8C, therein is illustrated a still further implementation of the present invention, but wherein the middle segment conductors of the Elements 10 do not run to alternate sides of the array. As may be seen from FIG. 8C, this implementation is similar to that of FIG. 8B, except that Bottom Ground Plane 76B is broken into two separate ground planes, identified as right Bottom Ground Plane 76RB and left Bottom Ground Plane 76LB, at one of the breaks or spaces between Middle Segment (MS) 14B and one of Outer Segments (OSs) 16RB or 16LB, thereby requiring separate conductors from the two parts of Bottom Ground Plane 76RB and 76LB and to the flex circuits. In addition, Middle Segment Conductor (MSC) 80 does not run to the edges of Element 10 between the piezoelectric layers as in FIG. 8B, but instead runs between Middle Segments (MSs) 14U and 14B to connect to the two Middle Segments (MSs) 14 in the manner described with regard to FIG. 8B, and then wraps around the edge of Middle Segment (MS) 14B at the break between Bottom Ground Planes 76RB and 76LB to the lower face of Middle Segment (MS) 14B. From that point, Middle Segment Conductor (MSC) 80 runs between the Bottom Ground Plane 76RB or 76LB and Backing Body 72 to the nearest edge of Element 10. As described above, and unlike the examples of FIGS. 9A and 9b, the Middle Segment Conductors (MSCs) 80 of successive Elements 10 do not run to alternate sides of the array, but always to the same side.

Figure 9A:
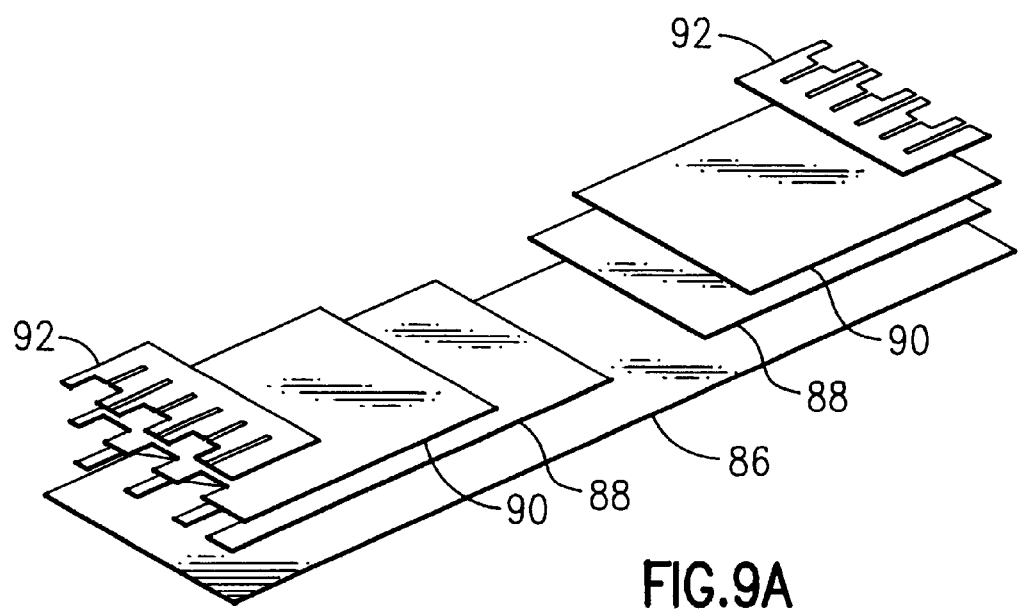
FIGS. 9A and 9B are diagrammatic representations of a connection assembly for a multiple aperture transducer.
Figure 9B:
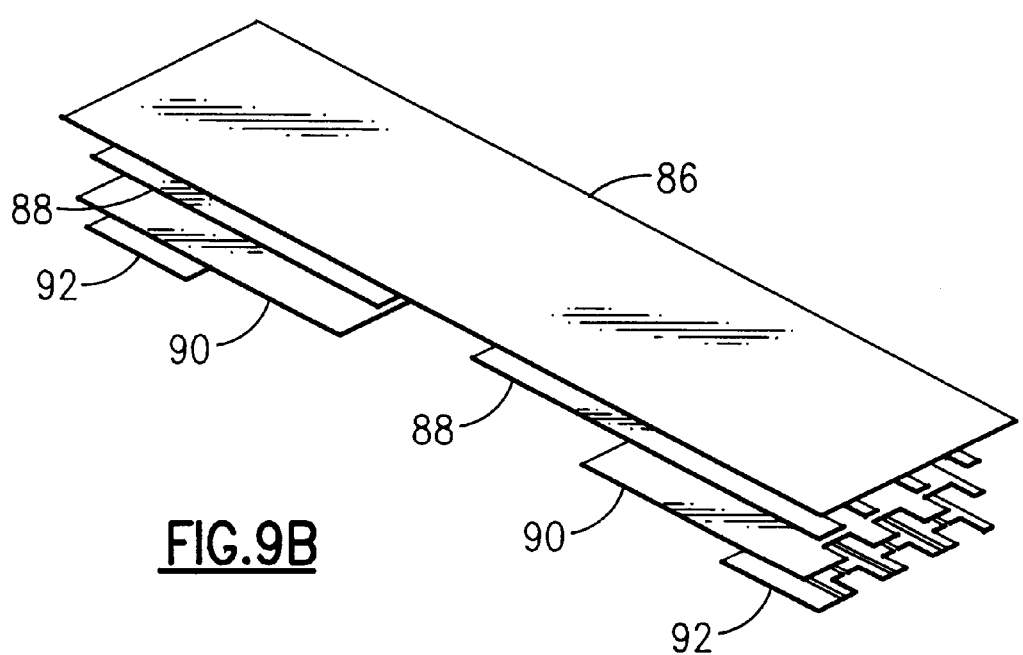

Referring finally to FIG. 8D, therein is shown an implementation of the present invention that is similar to that of FIG. 8C but wherein the Middle Conductor (MC) 80 of successive Elements 10 run to alternate sides of the array, as in the implementations illustrated in FIGS. 9A and 9B. As indicated therein, Bottom Ground Plane 76 is divided into three ground planes, respectively designated as Right Bottom Ground Plane 76RB, Left Bottom Ground Plane 76LB and Middle Bottom Ground Plane 76MB, at the breaks or separations between Middle Segment (MS) 14B and Outer Segments (OSs) 16LB and 16RB, thereby requiring that separate conductors be brought out from the three bottom ground planes to the edge of the array for connection to the flex circuits. As shown, two of the bottom ground plane conductors are taken out to one side and one to the other side.

Again, Middle Segment Conductor (MSC) 80 does not run to the edges of Element 10 between the piezoelectric layers as in FIG. 8B, but instead runs between Middle Segments (MSs) 14U and 14B to connect to the two Middle Segments (MSs) 14 in the manner described with regard to FIG. 8B, and then wraps around one edge of Middle Segment (MS) 14B at the break between Middle Bottom Ground Plane 76MB and the Right Bottom Ground Plane 76RB or Left Bottom Ground Plane 76LB at that edge of Middle Segment (MS) 14B, thereafter running between the Middle Bottom Ground Plane 76MB and the Right Bottom Ground Plane 76RB or Left Bottom Ground Plane 76L and that side and to the nearest edge of Element 10. In this implementation, Middle Segment Conductor (MSC) 80 will be brought out to the edge of the array in this manner on alternating sides of the array in each successive Element 10. In other implementations, and because both a Middle Segment Conductor (MSC) 80 and a Middle Bottom Ground Plane 76MB must be brought out for each Element 10, these two leads may be brought out to different edges of the array in each Element 10, so that the total number of leads going to each edge of the array are equal. In this regard, the Middle Segment Conductors (MSCs) 80 and the Middle Bottom Ground Planes 76MB may be brought out to the same edge of the array in each Element 10, or they may alternate for each successive Element 10.

It may therefore be seen from the above that the routing of middle segment leads, or conductors, to alternate sides of the array for successive elements or sub-elements along the array provides the maximum space for routing the middle segment and outer segment leads through the areas occupied by the outer segments. The routing method of the present invention thereby allows either or both of a greater number of segments in each element or a greater number of elements per unit length of the array, and thereby a higher resolution or higher frequency array.

2. Via Siting and Routing

It may be seen from the above examples of transducer structures that any conductor or pad areas that are located within the cross sectional areas of the transducer stack through which the dicing saw or other cutting tool passes to divide the piezoelectric material into segments, sub-segments and sub-elements will be cut apart, along the lines of the dicing cuts, from others of the conductor or pad areas. The cross sectional areas that are traversed by the dicing cuts are generally indicated in FIGS. 8A through 8D as those areas above Dicing Depth 82 and within Dicing Width 84. As indicated therein, Dicing Depth 82 extends downwards through the piezoelectric layers of the transducers to at least the bottom face of the lower piezoelectric layer and the electrode layer, and usually extends downwards at least through the insulator and connection layers adjacent to the piezoelectric layers and perhaps into the backing body, while Dicing Width 84 extends horizontally across the width of the piezoelectric layers of the transducer and may extend a significant distance beyond the physical edges of the piezoelectric layers.

It may also be seen that it is desirable to avoid the resulting loss of interconnections between, and connections to, the segments of the elements and sub-elements, particularly those to the middle segments, as the lost connections must subsequently be re-established by other connections, either in the flex circuits or by additional leads of pads in the thin film circuits.

The transducer connection assembly of the present invention avoids this problem by preserving at least selected groups of the connections originally provided in the thin film circuits, particularly those connecting to the middle segments, by placing these connections in the thin film circuit in a location outside the cross sectional areas traversed by the dicing tool, that is, in a location below Dicing Depth 82 or outside Dicing Width 84, or both below Dicing Depth 82 and outside Dicing Width 84.

Figure 10C:
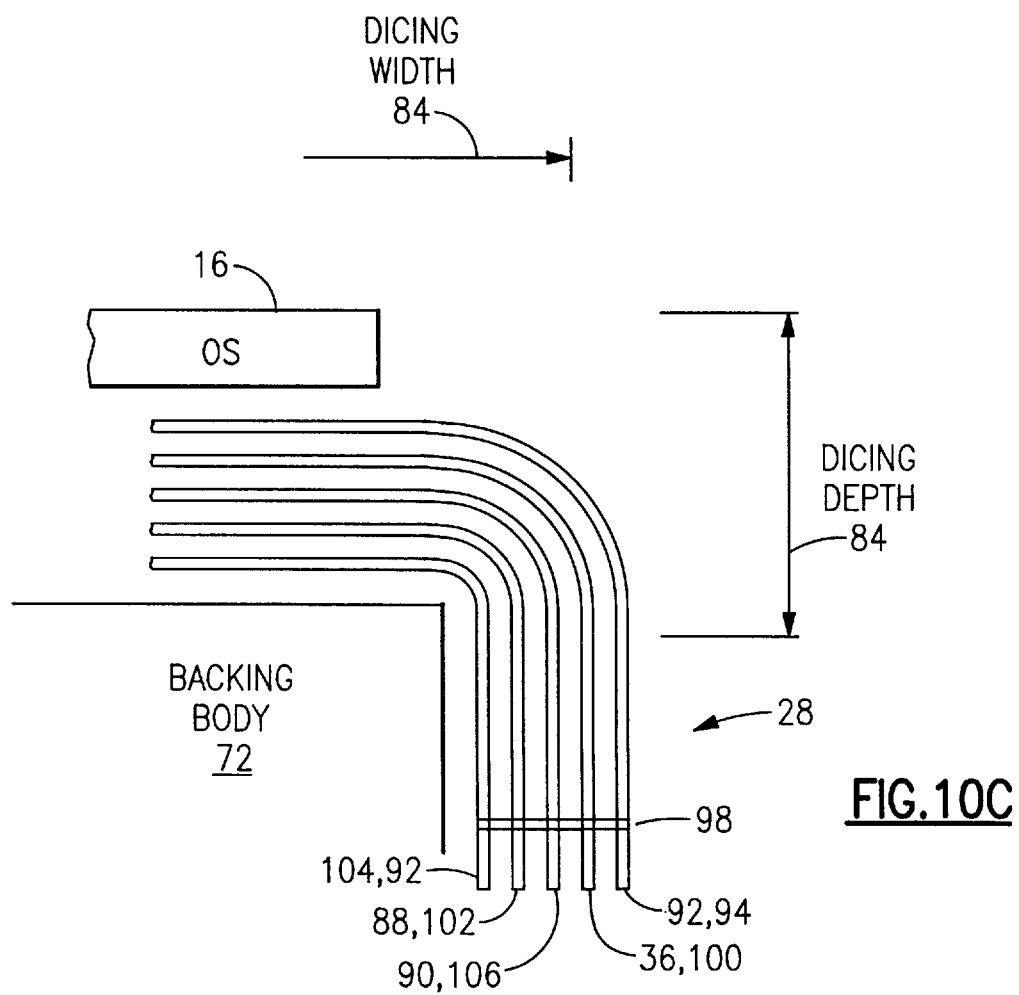
FIG. 10C is a diagrammatic representation of a connection assembly having reserved areas to preserve element connections during dicing.
Figure 10A:
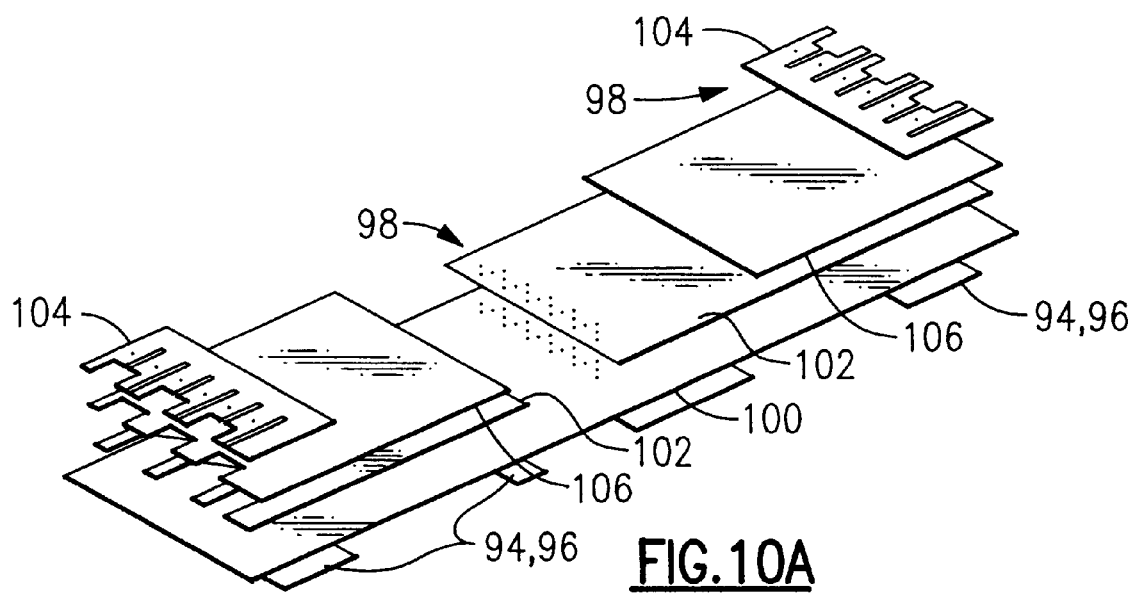
FIGS. 10A and 10B are diagrammatic representations of a connection assembly for a multiple aperture transducer.
Figure 10B:
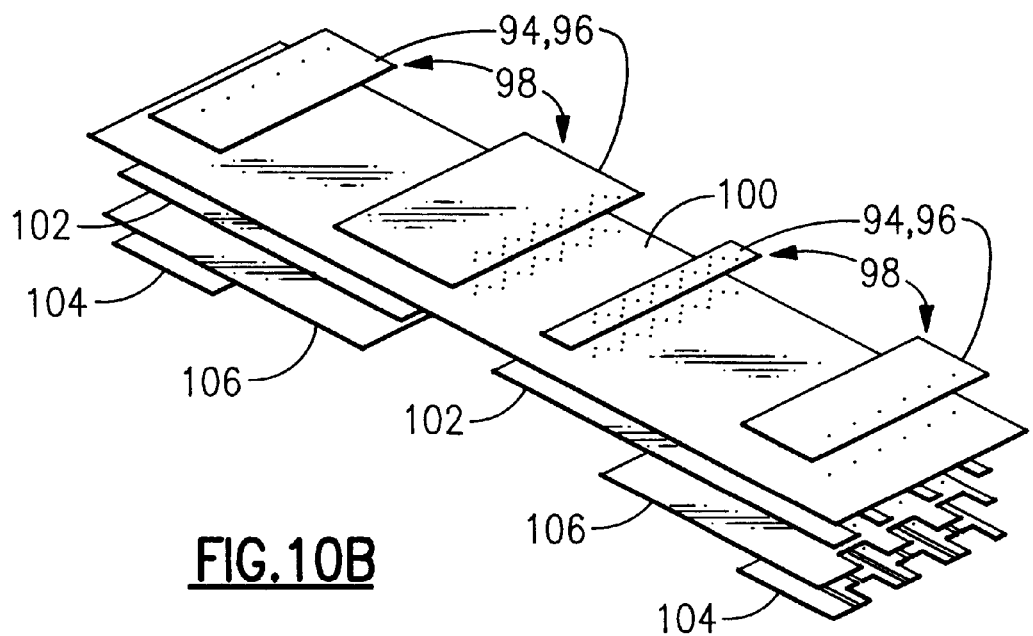

In this regard, FIGS. 9A and 9B illustrate the present invention for a transducer constructed from a single layer of piezoelectric material, as shown in FIG. 8A, while FIGS. 10A and 10B illustrate the present invention for a transducer constructed from two layers of piezoelectric material, as shown in FIGS. 8B through 8D, but may also represent the present invention for a single layer of piezoelectric material. FIG. 10C, in turn, illustrates the construction of the electrode, insulating layer and connection and pad layers of a transducer of the present invention so as to preserve certain of the connections made within the thin firm circuits.

Referring first to the single piezoelectric layer transducer of FIG. 8A, all of the connections to the middle segment and to the outer segments, except the connections to Upper Ground Plane 76U, are made on the lower faces of the piezoelectric segments, as has been described, and through the thin film circuits illustrated in FIGS. 9A and 9B. In this regard, it will be understood that FIGS. 9A and 9B illustrate the thin film circuit for a single element or sub-element of the transducer and that the circuitry shown in FIGS. 9A and 9B is repeated for the entire length of the transducer array as a single component made of the layers shown in FIGS. 9A and 9B. As shown in FIGS. 9A and 9B, this thin film circuitry, which together comprises a Connection Assembly 28, is comprised of a First Insulating Layer 86 which is directly adjacent the lower faces of the piezoelectric segments and a Connection Layer 88 which provides the connections to the middle segment and any outer segments not directly adjacent the edge of the array. A Second Insulating Layer 90 is superimposed over Connection Layer 88 and separates Connection Layer 88 from a Pad Layer 92, which provides the areas for connection to the flex circuits and may provide connections to the segments as necessary, such as connections to the outer segments adjacent the edges of the array. It will be understood that Insulating Layers 86 and 90, Connection Layer 88 and Pad Layer 92 are constructed in the same manner and from similar materials as those previously discussed herein above.

As is customary and well understood in the relevant arts, connections from the piezoelectric segments and to Connection Layer 88 or to Pad Layer 92 or between Connection Layer 88 and Pad Layer 92 are provided by vias running between the segments and the layers. As described, and as will be described in further detail below, a via is formed by a hole or opening form, for example, through an insulating layer such as First Insulating Layer 86, that is plated through with a conductive material such as a metal. As will also be described below, an array of via holes may be preformed in a layer and selected ones or groups of the holes plated through to provide connections where desired. For example, and referring to FIGS. 9A, 9B, 10A and 10B, the space required for connection pads can be reduced if Connection Layer 88 is arranged to pick up elements alternately. It will be noted that the vias are not illustrated in FIGS. 9A and 9B, for clarity and simplicity of representation, but are shown in FIGS. 10A and 10B.

As will be described below with reference to FIGS. 10A and 10B and FIG. 10C, the connections between the segments and between the segments and the flex circuits are made in a portion of Connection Layer 88 and/or Pad Layer 92 that are located below Dicing Depth 82 or outside Dicing Width 84, or both below Dicing Depth 82 and outside Dicing Width 84, so that the segments that are connected into a single electrical unit by Connection Layer 88 or Pad Layer 92, and other connections made through Connection Layer 88 or Pad Layer 92 at the time of assembly of the Connection Assembly 28 illustrated in FIGS. 9A and 9B to the piezoelectric layer remain intact during the subsequent dicing operations.

Finally with regard to the implementation illustrated in FIGS. 8A and 9A and 9B, it will be noted that Upper Ground Plane 76U is provided to make electrical contact with and between the upper faces of all of the piezoelectric segments, but is above Dicing Depth 82 and inside Dicing Depth 84 and would thereby be cut into separate areas during the dicing operation. According to the present invention, however, Upper Ground Plane 76U is assembled to the transducer array comprised of the piezoelectric layers and the Connection Assembly 28 after the dicing operation. As such, Upper Ground Plane 76U remains intact and makes common electrical contact with the upper faces of all of the segments of the transducer. It should also be noted that in the instance of a curved linear array Upper Ground Plane 76U is attached after the array has been curved and attached to the Backing Body 72, and thereby is fabricated with cut-outs and reliefs, as well understood in the arts, to lie flat against the faces of the segments when bent around the array.

Referring now to FIGS. 10A and 10B, the Connection Assembly 28 provided by the thin film circuits illustrated therein may be used, for example, in transducers having two piezoelectric layers, such as those illustrated in FIGS. 8B through 8D. It will be remembered from the above discussions that the connections for the implementation illustrated in FIG. 8B are made between the piezoelectric layers and are thus above Dicing Depth 82 and within Dicing Width 84 and that the connections for the implementations illustrated in FIGS. 8C and 8D, and in particular those for the critical middle segments, are made below the lower layer of piezoelectric material but are thus also probably above Dicing Depth 82 and within Dicing Width 84. Thus, while the Connection Assembly 28 and connection methods described below are advantageous when used with the implementations illustrated in FIG. 8B as well as in FIGS. 8C and 8D. The following will focus on the implementations illustrated in FIGS. 8C and 8D, however, as illustrating the full range of features of the present invention.

Therefore referring again to FIGS. 8C and 8D, it has been described above that the middle segments connections, as well as the outer segment connections, are routed below the lower face of the lower layer of piezoelectric material. This is accomplished, in particular with regard to the middle segments, by the use of wrap-around electrodes on the middle segments to bring any connections from the upper faces of the lower middle segments around to the lower faces of the middle segments.

This construction is reflected in the Connection Assembly 28 shown in FIGS. 10A and 10B wherein FIG. 10A is a view from the Backing Body 72 side of the Connection Assembly 28 while FIG. 10B is a view from the piezoelectric layer side of the Connection Assembly 28. As represented therein, the Connection Assembly 28 is comprised of an Electrode Layer 94 that includes four Electrode Areas 96 wherein the outer two of Electrode Areas 96 are directly adjacent and connect to the lower faces of Outer Segments (OSs) 16RB and 16LB while the inner two are directly adjacent to the lower face of Middle Segment (MS) 14B and located to connect to Middle Segment (MS) 14B's wrap-around electrode in the region of the two sides of Middle Segment (MS) 14B. As represented in FIGS. 10A and 10B, Electrode Areas 96 are provided with patterns of Vias 98.

The next layer of Connection Assembly 28 is a First Insulating Layer 100 that separates Electrode Layer 94 from a Connection Layer 102 that forms Middle Segment Conductors (MSCs) 80. Again, First Insulating Layer 100 and Connection Layer 102 are provided with patterns Vias 98 as necessary to pass connections between Electrode Layer 94 and Connection Layer 102. Connection Layer 102 is then separated from a Pad Layer 104 by a Second Insulating Layer 106, wherein Pad Layer 104 provides pads for electrical connection to the flex circuits as well as certain connections to Outer Segments (OSs) 16 and wherein Second Insulating Layer 106 and Pad Layer 104 are again provided with patterns of Vias 98 as necessary to provide connections between Pad Layer 104, Connection Layer 102 and Electrode Layer 94. Finally, it will again be understood that the Connection Assembly 28 illustrated in FIGS. 10A and 10B represents the Connection Assembly 28 for a single Element 10 or Sub-Element 56 and that the Connection Assembly 28 continues as a continuous structure the entire length of the array with the structure shown in FIGS. 10A and 10B being repeated for each element or sub-element.

Now considering the structure of a transducer connection assembly according to the present invention, it has been described above that any conductor or pad areas that are located within the cross sectional areas of the transducer stack through which the dicing saw or other cutting tool passes to divide the piezoelectric material into segments, sub-segments and sub-elements will be cut apart, along the lines of the dicing cuts, from others of the conductor or pad areas The cross sectional areas that are traversed by the dicing cuts were generally indicated in FIGS. 8A through 8A as those areas above Dicing Depth 82 and within Dicing Width 84. As described, the dicing cuts are made across the face of the transducer stack at each separation between elements, sub-segments or sub-elements and extend downwards through the piezoelectric layers of the transducers to at least the bottom face of the lower piezoelectric layer and the electrode layer, and usually at least through the insulator and connection layers adjacent to the piezoelectric layers and perhaps into the backing body. Each dicing cut extends horizontally across the width of the piezoelectric layers of the transducer and may extend a significant distance beyond the physical edges of the piezoelectric layers.

As was described, it is desirable to avoid the resulting loss of interconnections between, and connections to, the segments of the elements and sub-elements, particularly those to the middle segments, as the lost connections must subsequently be re-established by other connections, either in the flex circuits or by additional leads of pads in the thin film circuits. As also discussed, the transducer connection assembly of the present invention avoids this problem by preserving at least selected groups of the connections originally provided in the thin film circuits, particularly those connecting to the middle segments. According to the present invention, this is accomplished by placing these connections in the thin film circuit in a location outside the cross sectional areas traversed by the dicing tool, that is, in a location below Dicing Depth 82 or outside Dicing Width 84, or both below Dicing Depth 82 and outside Dicing Width 84.

Referring to the elements of the transducer assemblies illustrated in FIGS. 9A, 9B, 10A and 10B, it is shown in FIG. 10C that those portions of Connection Assembly 28 comprising the portions of Electrode Layers 94 and Electrode Areas 96, Insulating Layers 36,90,100,106, Connection Layers 88,102, and Pad Layers 92,104, with their associated Vias 98, that are located at the outer edges of the assembly, that is, at the outer edges of the piezoelectric layers, extend beyond the outer edges of the piezoelectric layers and are bent or turned downwards, that is, towards or along the backing body. These portions of Connection Assembly 28, which may be referred to as the "reserved areas" of Connection Assembly 28, are thereby located in an area of the assembly that is below Dicing Depth 82 or outside Dicing Width 84, or both below Dicing Depth 82 and outside Dicing Width 84. As such, the connections between the segments or sub-elements and between the segments or sub-elements and the flex circuits that are made in the reserved areas of Connection Assembly 28 are all below Dicing Depth 82 or outside Dicing Width 84, or both, so that all segments that are connected into a single electrical unit by the connection and/or pad layers, and all other connections made through the connection and pad layers to the piezoelectric layer during assembly of the transducer array in the reserved area of Connection Assembly 28 remain intact during the subsequent dicing operations.

Finally, it should be noted that the upper ground plane illustrated in FIGS. 8C and 8D is assembled to the transducer array comprised of the piezoelectric layers and the Connection Assembly 28 after the dicing operation. As such, the upper ground plane again remains intact and makes common electrical contact with the upper faces of all of the segments of the transducer. Again, in the instance of a curved linear array the upper ground plane is attached after the array has been curved and attached to the Backing Body 72, and thereby is fabricated with cutouts and reliefs, as well understood in the arts, to lie flat against the faces of the segments when bent around the array.

3. Via Patterns

It will be noted from FIGS. 10A and 10B that at least some of Vias 98, most particularly those associated with the connections to Middle Segments (MSs) 14U and 14B, are not formed as rows of single Vias 98, but instead are formed in closely spaced and staggered patterns. The Vias 98 are spaced sufficiently far enough apart in the pattern to provide the necessary width between the Vias 98 to form the signal conductors, that is, a distance in the range of 10 $\mu$m to 3 mils, and are staggered so that the separation between Vias 98 along the axis perpendicular to the lines along which the assembly is diced is approximately the width of a single Via 98.

The Vias 98 in each pattern will thereby provide a corresponding pattern of connections, for example, between the middle segment wrap-around electrode and a Connection Layer 102, such that at least sufficient connections will remain after the dicing of the assembly, and the consequent severing of the Via 98 connections intersected by the slices, to form the necessary connections independently of the precise alignment of the layers, particularly Electrode Layer 94, Connection Layer 102 and Pad Layer 104, and the dicing lines along which the piezoelectric material is sliced into segments, elements and sub-elements. This method of constructing Vias 98 is therefore advantageous in that the alignment of the electrode, connection and pad layers, the blocks of piezoelectric material and the dicing mechanism are not critical, thereby allowing easier and less expensive construction and assembly of the transducer.

Further in this regard, it should be noted that the manufacture of the thin film circuits comprising Connection Assemblies 28 and particularly the assembly of the layer of a Connection Assembly 28 and the assembly of the Connection Assembly 28 to the block or blocks of piezoelectric material typically requires careful alignment of the individual components in each step of the process. This can be difficult, however, as the thin film circuits comprising a Connection Assembly 28 and the Connection Assembly 28 are not rigid and are therefore difficult to handle and align.

According to the present invention, however, this problem is addressed by constructing the Connection Assembly 28 on a Carrier 70, and then either leaving the Carrier 70 in place as a part of Backing Body 72 or removing the Carrier 70 by one of the methods previously mentioned, for example, after the Connection Assembly 28 has been assembled to the piezoelectric material or after the piezoelectric material has been diced.

4. Construction of Vias

Figure 11B:
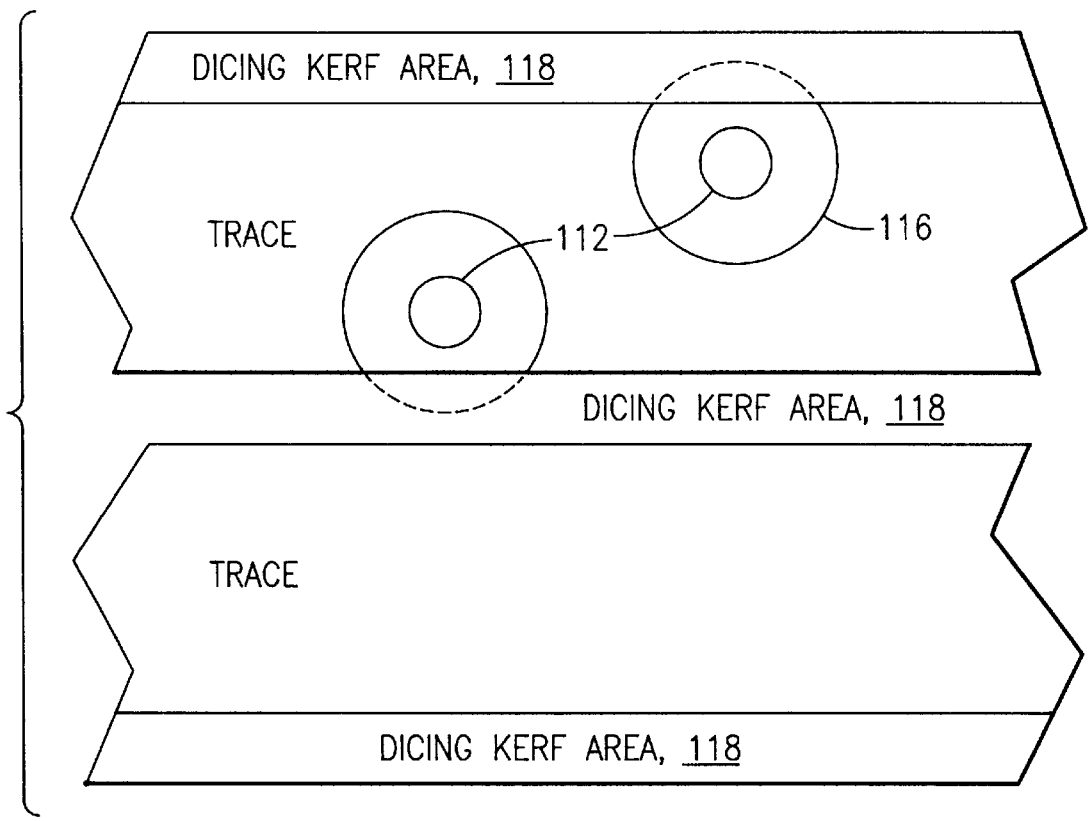
FIGS. 11A and 11B are cross sectional view of a via construction.
Figure 11A:
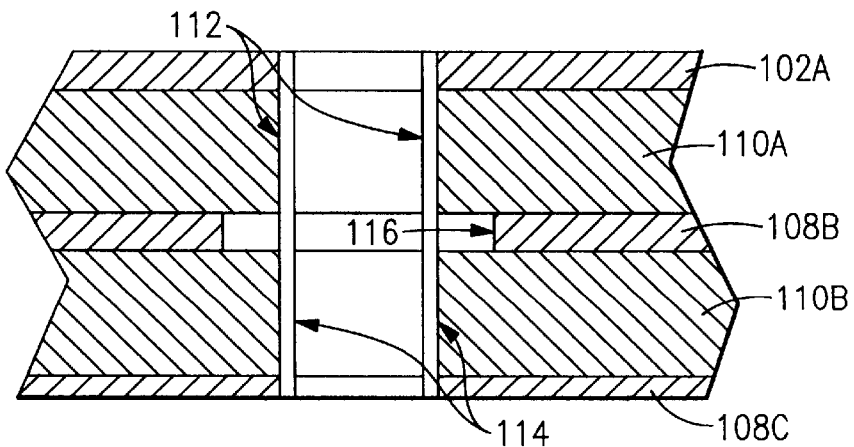

The method of selectively interconnecting between conductive layers of a multilayer thin film circuit by vias has been described briefly above, and is illustrated further in FIGS. 11A and 11B, which are respectively a plane view and a cross section view of a multilayer thin film circuit as may be constructed for an ultrasonic transducer. As represented therein, the exemplary circuit is comprised of Conductive Layers 108A, 108B and 108C separated by Insulating Layers 110A and 110B and is thus comparable to the Connection Assemblies 28 previously discussed.

An exemplary Via 98 connecting Conductive Layers 108A and 108C is formed by a Via Hole 112 extending through Conductive Layer 108A, Insulating Layer 110A, Conductive Layer 108B, Insulating Layer 110B and Conductive Layer 108C and internally plated through with a Conductive Material 114, such as a metal compatible with the materials of Conductive Layers 108A, 108B and 108C. Whether a given one of the conductive planes is connected to the Via 98, and this to any of the other conductive planes that are connected to the Via 98, is determined and controlled by the size of Via Hole 112 where it passes through the plane. Briefly, if a given conductive plane is not to be connected to the Via 98, the Via Hole 112 in that plane is formed in a larger diameter as a Clearance Hole 116, whereupon the plating process will not bridge the gap formed by Clearance Hole 116 to connect the conducting plane to the Conductive Material 114.

A recurring problem with this method of interconnecting the conductive planes in a thin film Connection Assembly 28, however, is that Clearance Holes 116 require more space than do the connective openings, which are generally of the diameter of Via Hole 112, which in turn are generally narrower than the width of any connector leads formed on the conductive player. That is, in transducers having a small Element 10 or Sub-Element 56 pitch, that is, where the elements or sub-elements are relatively narrow as in a very high frequency or very high resolution transducer, the space available for connector leads and vias in the width of each Element 10 or Sub-Element 56 is relatively small. This problem is accented when the Element 10 or Sub-Element 56 contains several segments. It is possible, in fact, that either the conductive leads formed in a conductive plane will be of insufficient width when the width required for Clearance Holes 116 is subtracted from the width available for running of the Elements 10 or Sub-Elements 56, or that there will be insufficient width for any Clearance Holes 116 after the conductive leads have been formed.

According to the present invention as illustrated in FIG. 11A, however, all Vias 98 and their associated Clearance Holes 116, if any, are located within the areas of the conductive planes defined by Elements 10 or Sub-Elements 56, but adjacent the edges of the areas occupied by the Elements 10 or Sub-Elements 56, so that Clearance Holes 116, if any, extend into the Dicing Kerf Areas 118 between the Elements 10 or Sub-Elements 56. As such, this portion of each Clearance Hole 116, which contains material that is to be removed from the conductive plane in any event, is cut away when the transducer assembly including the connector assembly is diced.

In a further aspect of the present invention, as illustrated in FIG. 11A, each conductor lead on a given plane, and any corresponding conductor leads on other conductive planes of the thin film assembly, are provided with more than one Via 98, with the Vias 98 staggered, as has been illustrated in FIGS. 10A and 10B, so that a misalignment of the thin film circuit with respect to a Dicing Kerf Area 118 that results in the dicing cutting into one Via 98 will leave the other Vias 98 untouched and intact.

Once again, it will be apparent that the design and construction of a multiple aperture transducer as discussed above is exemplary and that other arrangements of transducer segments, sub-elements, electrode areas, and insulating and connection layers, are possible and fall within the design and construction principles described herein above. For example, a given element need not be constructed with an odd number of segments or sub-elements but may be constructed and connected as described above with an even number of segments or sub-elements. Also, the arrangement and dimensions of the segments or sub-elements and the corresponding layouts of the insulating and connection layers need not be symmetric, either about the longitudinal center line of the array or with respect to one another. Again, it will be recognized by those of skill in the arts that the insulating and connection layers may each or both be comprised of multiple layers and that the layers of insulating and connection layers may be interleaved as necessary to isolate the connections from one another and from the electrodes.

Lastly, while the invention has been particularly shown and described with reference to preferred embodiments of the apparatus and methods thereof, it will be also understood by those of ordinary skill in the art that various changes, variations and modifications in form, details and implementation may be made therein, as has been discussed herein above, without departing from the spirit and scope of the invention as defined by the appended claims. Therefore, it is the object of the appended claims to cover all such variation and modifications of the invention as come within the true spirit and scope of the invention.

What is claimed is:

1. A multiple aperture ultrasonic transducer including a linear array of transmitting and receiving elements wherein each element is comprised of a middle segment and at least one pair of outer segments, the middle segment and outer segments forming apertures of the array, and a connection assembly for interconnecting the outer segments of each element and for connecting the segments of each element to transmit/receive circuits, the connection assembly comprising:

for each element of the array, an electrode layer located directly adjacent the segments of the element and having an electrode area corresponding to each segment of the element, each electrode area being located adjacent to and connecting to the corresponding segment, an insulating layer superimposed on the electrode layer and having a segment to segment connection opening corresponding to and located within the electrode area of each outer segment, a segment to segment connection area for and corresponding to each pair of outer segments forming an aperture, each segment to segment connection area extending between the segment to segment connection openings of the pair of outer segments, a middle segment connection opening corresponding to and located within the electrode area of the middle segment, a middle segment connection area extending from the middle segment connection opening and to an edge of the element, and a connection layer superimposed on the insulating area and having a middle segment connector connected to the middle segment electrode and extending from the middle segment connection opening and across the middle segment connection area to a pad at the edge of the element to connect to a transmit/receive circuit, and for each pair of outer segments forming an aperture, a segment to segment connector extending across the segment to segment connection area of the outer segments and connected to the electrode areas of the outer segments and to a pad at the edge of the element to connect to a transmit/receive circuit.

2. The multiple aperture ultrasonic transducer of claim 1 wherein each element is divided into sub-elements and wherein:
- one half of the segments of each sub-element and the connection assembly connections thereto are offset along the length of the array by one sub-element relative to the other half of the segments of the sub-element, and
- the order of the pads connecting the middle segment and outer segment conductors to the transmit/receive circuits are reversed on alternate sub-elements.

3. The multiple aperture transducer of claim 1 wherein the middle segment connector of successive elements along the linear array are routed to alternate edges of the linear array.

4. The multiple aperture transducer of claim 1 wherein:
- the connection assembly is constructed on a carrier,
- the carrier and connection assembly are assembled to the transmitting and receiving elements, and
- the carrier and connection assembly are assembled to a backing body so that the carrier is a mechanical and acoustic element of the transducer structures.

5. The multiple aperture transducer of claim 1 wherein:
- the connection assembly is constructed on a carrier,
- the carrier and connection assembly are assembled to the transmitting and receiving elements,
- the carrier is removed from the connection assembly, and
- the connection assembly and transmitting and receiving elements are assembled to a backing body.

6. The multiple aperture transducer of claim 1 wherein:
- the electrode layer, the insulating layer and the connector layer are formed by deposition process onto a matching layer carrier comprised of a material having acoustic properties to function as a matching layer of the transducer and the matching layer carrier with the electrode layer, the insulating layer and the connector layer are assembled to a transmitting and receiving face of the transducer to function as a matching layer.

7. The multiple aperture transducer of claim 1, wherein:
- the electrode layer, the insulating layer and the connector layer are formed by deposition process onto the transmitting and receiving elements.

8. The multiple aperture transducer of claim 1 wherein the elements are initially constructed of a monolithic block of transducer element material and wherein the connection assembly is initially fabricated as a single assembly including the electrode layer, insulating layer and connection layer for all elements of the transducer that is assembled to the monolithic block and wherein the monolithic block of transducer element material is thereafter diced into the individual elements of the linear array by dicing the assembly of the monolithic block and transducer element material and the connection assembly across the width of the array in cross sectional dicing areas bounded by a predetermined dicing depth and a predetermined dicing width, the connection assembly further comprising:
- a plurality of vias for connecting the electrode areas of the segments to the corresponding connectors of the connector layer, wherein
  - a first area of the electrode layer, the insulating layer and the connector layer are within the dicing areas,
  - a reserved portion of at least the insulating and connector layers is located in a cross section area outside the dicing area,
- so that the connections formed between the electrode areas of the segments and from the electrode areas to the pads in the reserved area of the connector layer remain intact.

9. The multiple aperture transducer of claim 8 wherein each element of the linear array is comprised of at least two layers of transducer material with an interlayer electrode layer between the layers of transducer material and with interlayer electrode areas formed in the interlayer electrode layer and connecting middle segments of the elements through interlayer vias with the layers of the connection assembly, wherein:
- the interlayer vias are located along the edges of the middle segments to connect with the interlayer electrode layer connecting to the middle segments, and are arrayed in staggered patterns, so that when the layers of transducer material are diced into the elements of the linear array, at least one interlayer via connected to each middle segment will remain intact.

10. The multiple aperture transducer of claim 9 wherein interlayer vias remain unconnected to selected layers of the connection assembly by forming clearance holes around the interlayer vias where the interlayer vias pass through the selected layers and wherein the interlayer vias having clearance holes are located adjacent the edges of the electrode areas so that each clearance hole extends into a dicing kerf between the elements.

\* \* \* \* \*